United States Patent
Elias et al.

(10) Patent No.: US 6,395,709 B1
(45) Date of Patent: *May 28, 2002

(54) METHODS AND COMPOSITIONS FOR STIMULATING TISSUE GROWTH AND EPITHELIAL MOISTURIZATION

(75) Inventors: Peter Michael Elias, Mill Valley; Walter Martin Holleran, San Rafael, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/483,510

(22) Filed: Jan. 14, 2000

Related U.S. Application Data

(62) Division of application No. 08/333,852, filed on Nov. 3, 1994, now Pat. No. 6,054,433.

(51) Int. Cl.[7] ............... A61K 31/70; A61K 31/045; A61K 31/44
(52) U.S. Cl. ............... 514/25; 514/35; 514/54; 514/299; 514/729
(58) Field of Search ............... 514/25, 35, 54, 514/299, 729

(56) References Cited

U.S. PATENT DOCUMENTS 6,054,433 A * 9/2000 Elias et al. ............... 514/25

* cited by examiner

*Primary Examiner*—Elli Peselev
(74) *Attorney, Agent, or Firm*—Townsend and Townsend and Crew LLP

(57) ABSTRACT

The invention herein encompasses methods effective to stimulate epithelial cell proliferation and/or enhance epithelial moisturization and lubrication in a mammalian subject utilizing a composition comprising one or more inhibitors of β-glucosidase activity or β-glucocerebrosidase activity. The composition of the method may alternatively comprise a glycosphingolipid, particularly glucocerebroside, or a combination of the above inhibitor(s) and a glycosphingolipid. The method is effective to enhance the cosmetic appearance of skin and promote healing of skin and mucous membranes damaged or deficient from aging, traumatic wounds, photoaging and a variety of atrophic conditions.

The method may be applied to cells in culture. Also included in the invention is a composition comprising one or more inhibitors of β-glucosidase and a glycosphingolipid useful to stimulate cell proliferation and enhance tissue moisturization and lubrication.

30 Claims, 30 Drawing Sheets

Fig. 3
β-Glucocerebrosidase Inhibitors
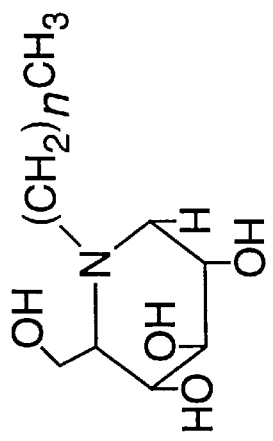
DEOXY-NOJIRIMYCIN
dNJM
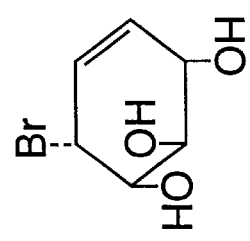
BROMOCONDURITOL
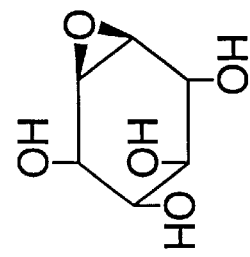
CONDURITOL B EPOXIDE
CBE
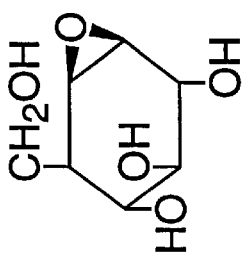
BROMOCONDURITOL B EPOXIDE
BrCBE
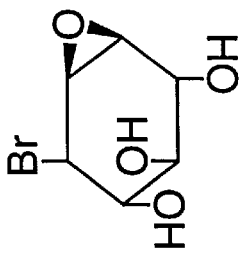
CYCLOPHELLITOL N-Hexylglucosylsphingosine (N-Octanoyl)

β-Xyloside

4-Methylumbelliferyl-β-D-xyloside

Fig. 8
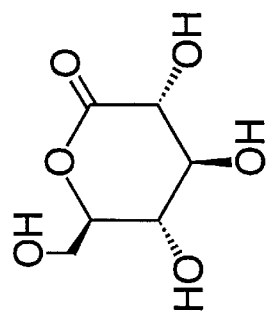
D-GLUCONO-1,5-LACTONE
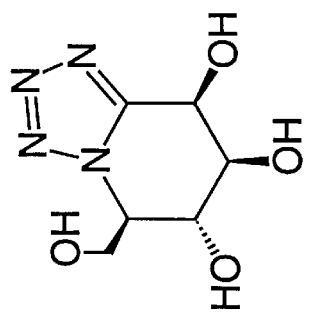
D-MANNONOJIRITETRAZOLE
(D-Mannotetrahydro-
pyrido[1,2-d]tetrazole)
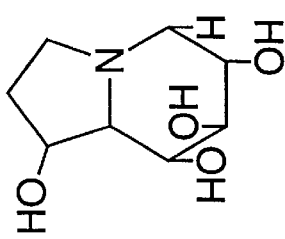
CASTANOSPERMINE
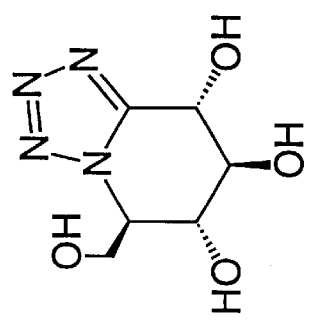
D-GLUCONOJIRITETRAZOLE
(D-Glucotetrahydro-
pyrido[1,2-d]tetrazole)

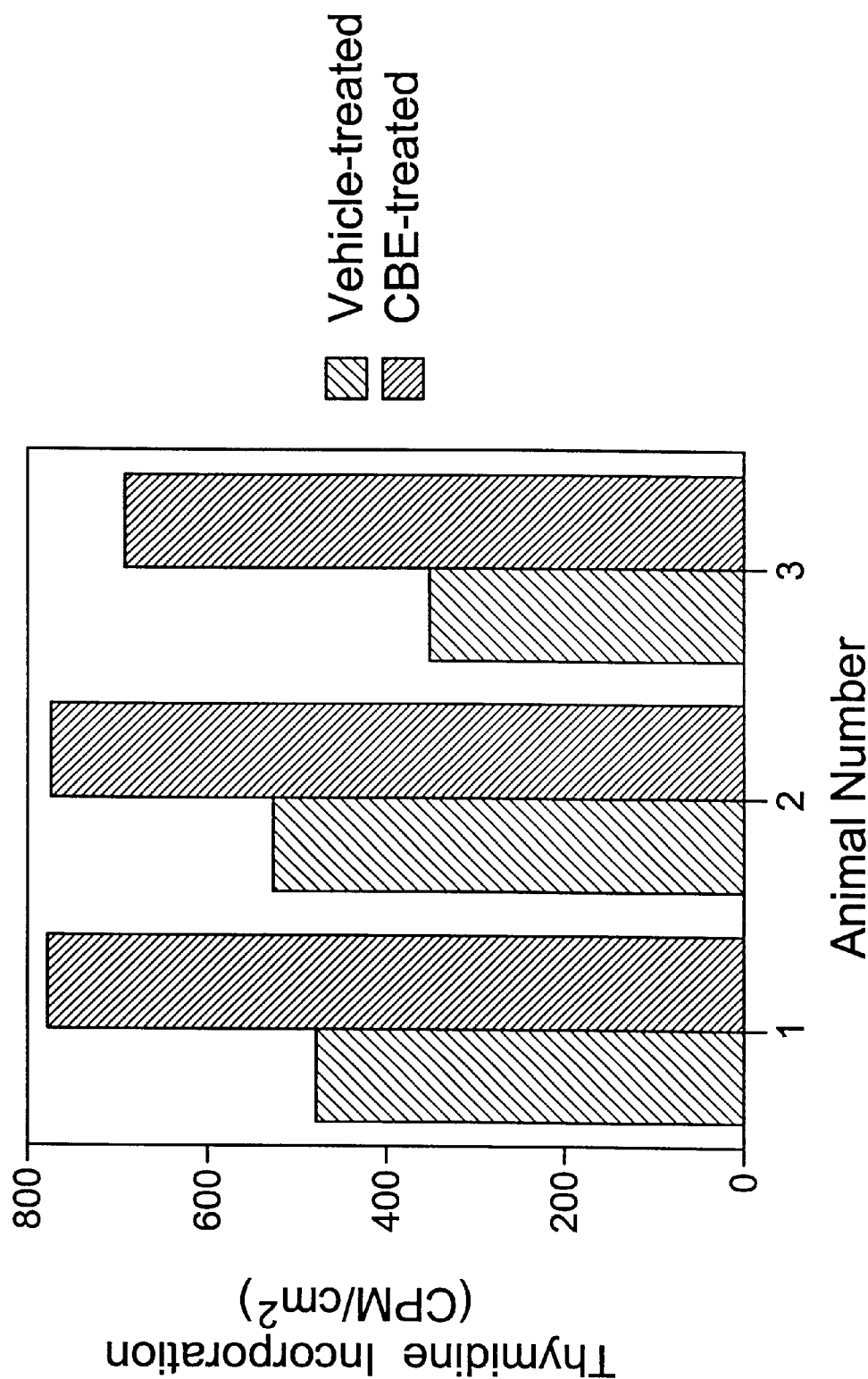

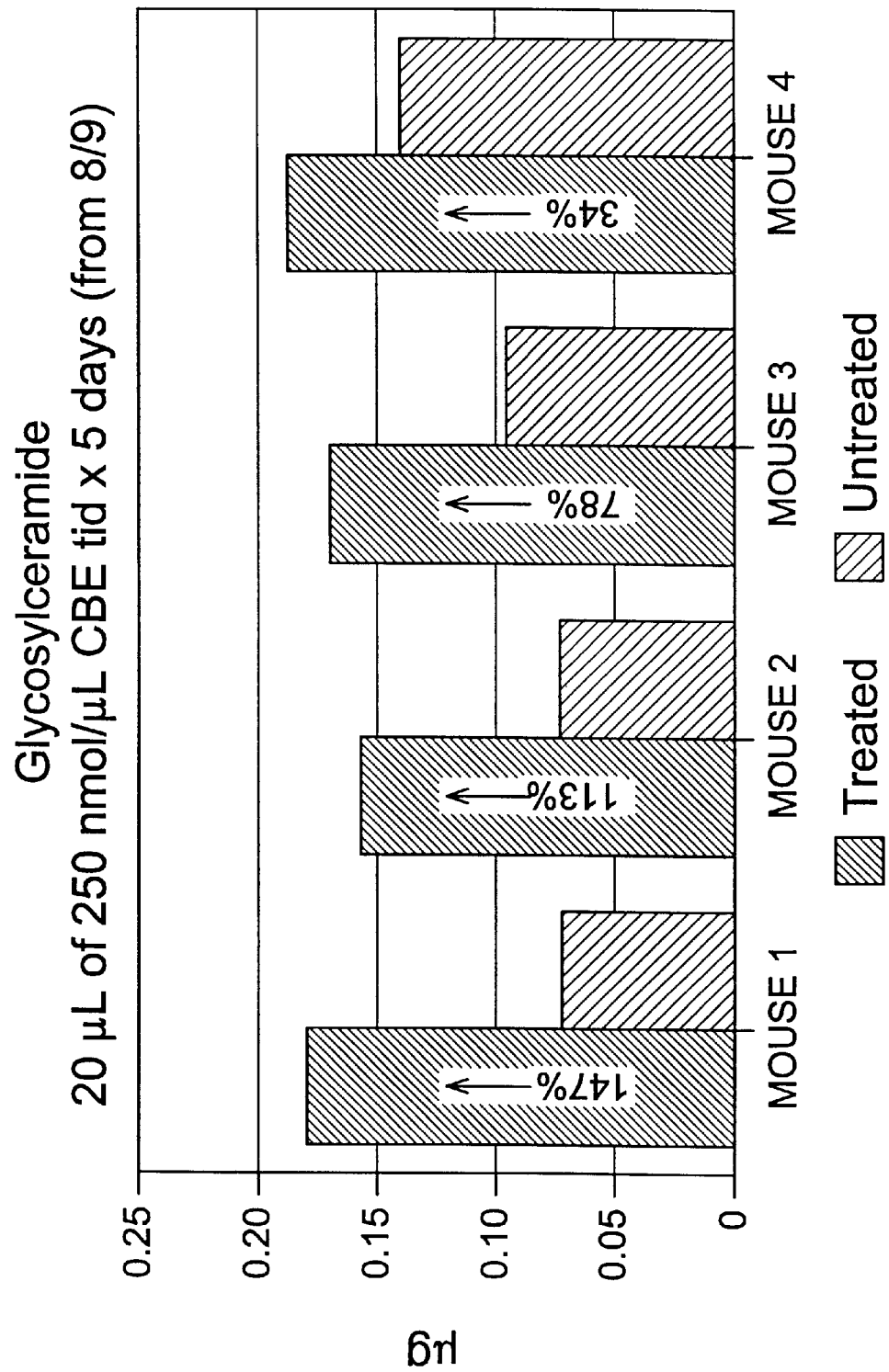

METHODS AND COMPOSITIONS FOR STIMULATING TISSUE GROWTH AND EPITHELIAL MOISTURIZATION

This application is a division of and claims the benefit of U.S. patent application Ser. No. 08/333,852, filed Nov. 3, 1994, the disclosure of which is incorporated by reference, now U.S. Pat. No. 6,054,433.

BACKGROUND OF THE INVENTION

This invention was developed at least partially with United States Government support under Grant No. AR 19098 from the National Institutes of Health and Grant No. AR39448 from the United States Public Health Service. The United States Government may have rights in this invention.

1. Field of the Invention

This invention relates to novel cosmetic and therapeutic methods for stimulating tissue growth and/or enhancing moisturization and lubrication in mammalian epithelium, such as skin and mucous membrane. The methods comprises providing to an individual a composition comprising at least one inhibitor of β-glucosidase activity, a glycosphingolipid or the combination of a β-glucosidase inhibitor with a glycosphingolipid.

2. Description of Related Art

Mammalian keratinizing epithelium, including the epidermis and various mucous membranes, provide protection against the invasion of microorganisms, physical trauma, toxic chemicals, and particularly loss of bodily fluids, i.e., a permeability barrier function. This barrier function derives from a combination of physical impenetrability, resilience, resistence to traumatic force, and its relative impermeability to water, attributable to a unique mixture of lipids within the outermost layer of skin, the stratum corneum.

Injuries to the skin barrier may occur from thermal burns, penetrating wounds, exposure to organic solvent, surfactants/detergents and a variety of irritating chemicals, and in a variety of blistering skin diseases. The repair of epidermal damage requires proliferation of basal cells to replace damaged cells. Because of limitations in the proliferative capacity of the epidermis the treatment of substantial damage to skin may require skin grafting for optimal recovery. Moreover the repair of skin damage becomes less than optimal with chronological or photoaging of skin, with immunosuppressed conditions, in patients with chronic diseases, such as cancer and as a consequence of therapy with some types of drugs. A further consequence of an insufficient proliferative capacity is an increased susceptibility to injuries with repetitive insults to the skin.

Among major cosmetic and therapeutic concerns are the age-and sun-associated changes that occur in the skin, such as wrinkling, thinning and increased susceptibility to injury. Thinning, brittle skin also results from abnormal hydration and alterations in hormonal levels resulting from the aging process. The stimulation of proliferation in skin and hair follicles has been attempted with steroidal compounds. (Palacios, H. J., U.S. Pat. No. 5,256,406) Retinoid-related compounds have also been used to treat sun damaged skin. (Kligman, A. M., U.S. Pat. No. 4,877,8050) However, previous methods have been only partially effective or subject to deleterious side effects.

Other epithelial tissues, such as mucous membranes, can also become compromised with aging, in individuals suffering from nutritional deficiency syndromes, and in postmenopausal hormone deficiency. These alterations can result in thin, dry, fragile, and/or atrophic mucous membrane. Ocular membranes especially exhibit reduced lubricating fluids with age and a variety of ophthalmic pathologies.

A major function particularly of both the epidermis and mucosal epithelia is to provide a barrier that prevents excessive loss of body fluids. This epithelial barrier is mediated by a system of multilayered membrane lipid-enriched bilayers that exist throughout the intercellular spaces of the stratum corneum in the epidermis and keratinizing mucous membranes. These multiple bilayers derive from lipids and proteins secreted from cells in the outer epidermis. These cells are in turn the products of the underlying proliferative basal cells.

The bilayers in the stratum corneum of epidermis are enriched in an approximately equimolar mixture of three major lipid species: ceramides (CER), free fatty acids, and cholesterol. The multilayered bilayers in keratinizing mucosal epithelia consist of approximately equimolar ratios of glucosylceramides (GlcCER), free fatty acids and cholesterol.

Of the three key lipids comprising the barrier, the ceramides comprise the greatest quantity (40–50%. by weight). Ceramides form the precursor/backbone of glucosylceramides (GlcCER), more complex glycosphingolipids (GSLs), and sphingomyelin (SM) (FIGS. 1+2).

Glycosphingolipids include gangliosides, globosides, and sulfatides. Gangliosides are glycosphingolipids containing at least one sialic acid (SA) bound to the ceramide core structure (FIG. 2). An example is $GM_1$, a mono-sialic acid ganglioside. Sulfatides are glycosphingolipids with at least one sulfated oligosaccharide bound to the ceramide core structure. (Hakomori, S.-I. (1983), "Chemistry of Glycosphingolipids", p. 1–165, in *Sphingolipid Biochemistry* J. N. Kanfu and S.-I. Hakomori, eds., Plenum Press, New York, N.Y.

In addition to their role in the epidermal permeability barrier, alterations in sphingolipid metabolism have been implicated in disease pathogenesis. In Gaucher's disease, impaired glucocerebrosidase (GlcCER'ase) activity results in organomegaly. Tissue hyperplasia is associated with the accumulation of lipids, including GlcCER, within several tissues (e.g., liver, spleen) (Barranger, J. A., Ginns, E. I., Glucosylceramide Lipidoses: Gaucher Disease in *Metabolic Basis of Inherited Disease*. (1989), p. 1677, McGraw Hill Inc., New York, N.Y.)

The abnormalities in Gaucher's disease point to disorder of GlcCER-CER metabolism as the cause of the tissue hyperplasia. A role for excess GlcCER is supported by the observation that injection of emulsified GlcCER into mice induces Gaucher-type hepatic hypertrophy. (S. C. Datta and N. S. Radin, Lipids 23:508–510 (1988)) Moreover, Gaucher's disease is simulated with systemic administration of the specific inhibitor of GlcCER'ase, bromo-conduritol-B-epoxide to mice. Along with the elevations in cellular GlcCER content, hyperplasia of the brain and liver was observed (Hara, A., Radin, N. S., Biochim. Biophys. Acta 582:423–433 (1979). Furthermore, the epidermis in mucosal epithelia displays a preponderance of GlcCER and depletion of CER in association with depletion of β-glucosidase activity (Squier, C. A., et al. Arch. Oral Biol. 31:741–747 (1986).

Finally exposure of cultured MDCK cells (kidney) to conduritol-B-epoxide results in a time-dependent accumulation of GlcCER with a parallel increase in cellular proliferation (Shayman, J. A. et al., J. Biol. Chem. 266:22968–22978 (1991)). Thus increased GlcCER levels have been associated with pathological organomegaly in susceptible organs, with proliferation in cultured cells and the normal formation of mucosal surfaces. However epidermal structures are typically not associated with GlcCER-sensitive disease states, such as Gaucher's disease.

Accordingly there is still a need for a safe and effective method that will both enhance epithelial growth and restore a smooth, pliant, flexible, well-lubricated surface to the stratum corneum and mucous membranes, includig the conjuctivae of the eye.

SUMMRY OF THE INVENTION

The invention herein encompasses a method effective to stimulate cell proliferation and enhance epithelial moisturization and lubrication of mammalian subject or mammalian cells wherein a composition comprising one or more inhibitors of β-glucosidase activity, a glycosphingolipid or a combination of one or more inhibitors of β-glucosidase and a glycosphingolipid is administered to the subject or cell.

The invention further includes a method effective to enhance epithelial moisturization and lubrication and separately encompasses a method effective to stimulate cell proliferation wherein a composition comprising one or more inhibitors of β-glucosidase, a glycosphingolipidor a combination of one or more inhibitors of β-glucosidase and a glycosphingolipid is administered to a subject.

Also included in this invention is a composition comprising one or more inhibitors of β-glucosidase and a glycosphingolipid useful to stimulate cell proliferation and enhance tissue moisturization and lubrication.

The above features and advantages of this invention will be more fully understood by reference to the following detailed description and the drawings.

BRIEF DESCRIPTION OF THE DRAWINGS AND TABLES

FIG. 1 diagrams the pathway of ceramide metabolism.

FIG. 2 demonstrates the structural relationship of major sphingolipids.

FIG. 3 provides the structure of conduritol-type inhibitors of β-glucocerebrosidase.

FIG. 4 provides the structure of N-acylglucosylsphingosine.

FIG. 5 provides the structure of ceramide.

FIG. 6 provides the structure of xylosides.

FIG. 7 provides the structure of 4-methylumbelliferyl-xyloside.

FIG. 8 provides the structures of castanospermine, D-glucono-1,5-lactone, D-gluconojiritetrazole and D-mannonojiritetrazole.

FIG. 17 shows the effect of topical CBE application on epidermal proliferation.

FIG. 24 (A&B) compares the effect of a variety of inhibitors of β-glucocerebrosidase on DNA synthesis.

Figure 25:
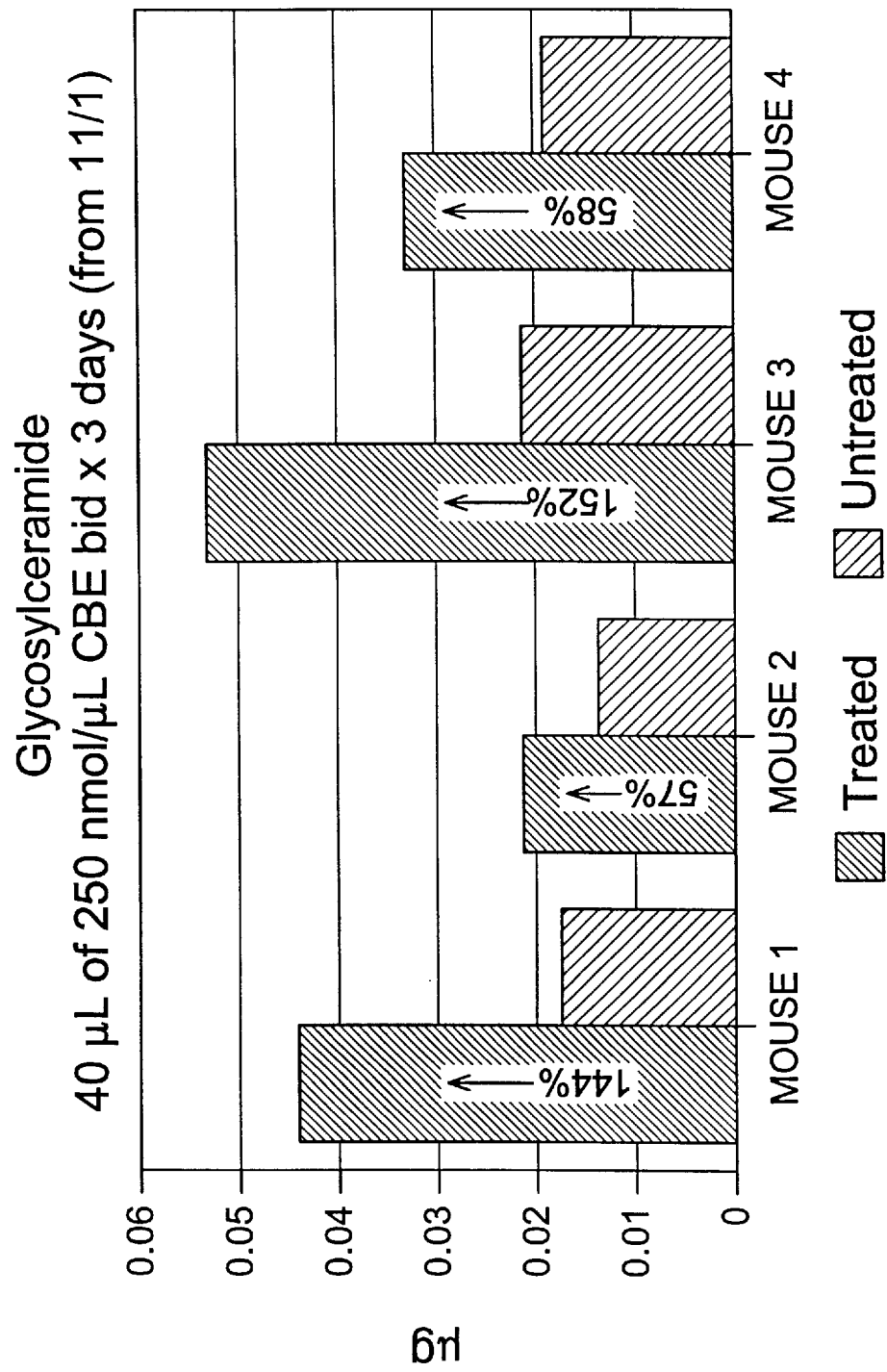

FIG. 25 shows the effect of occlusion on thymidine incorporation in CBE- and glucosylceramide-treated and control murine epidermis.

Figure 26:
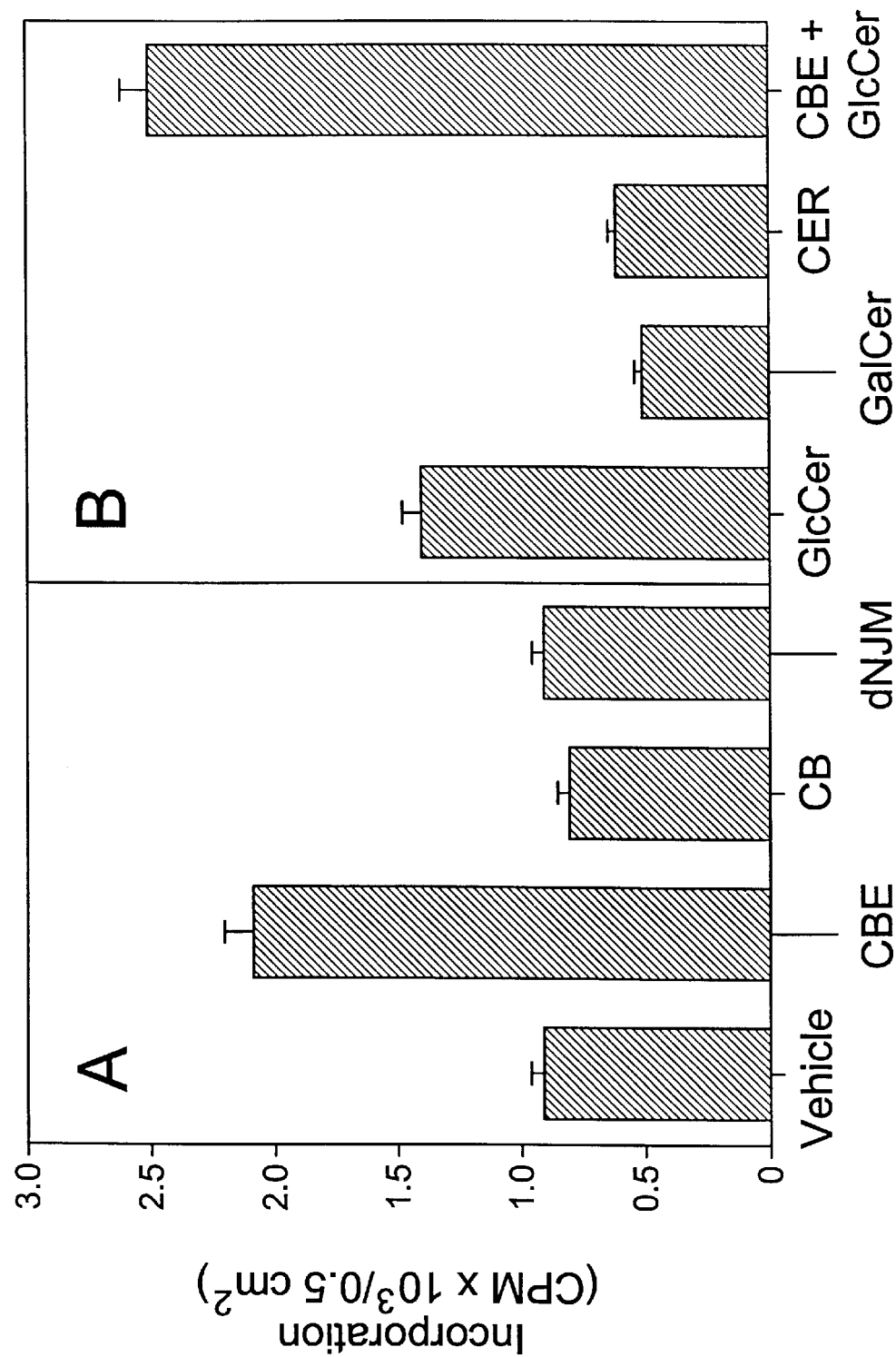

FIG. 26 shows the effect of methylumbelliferyl-xyloside of barrier recovery.

Figure 27:
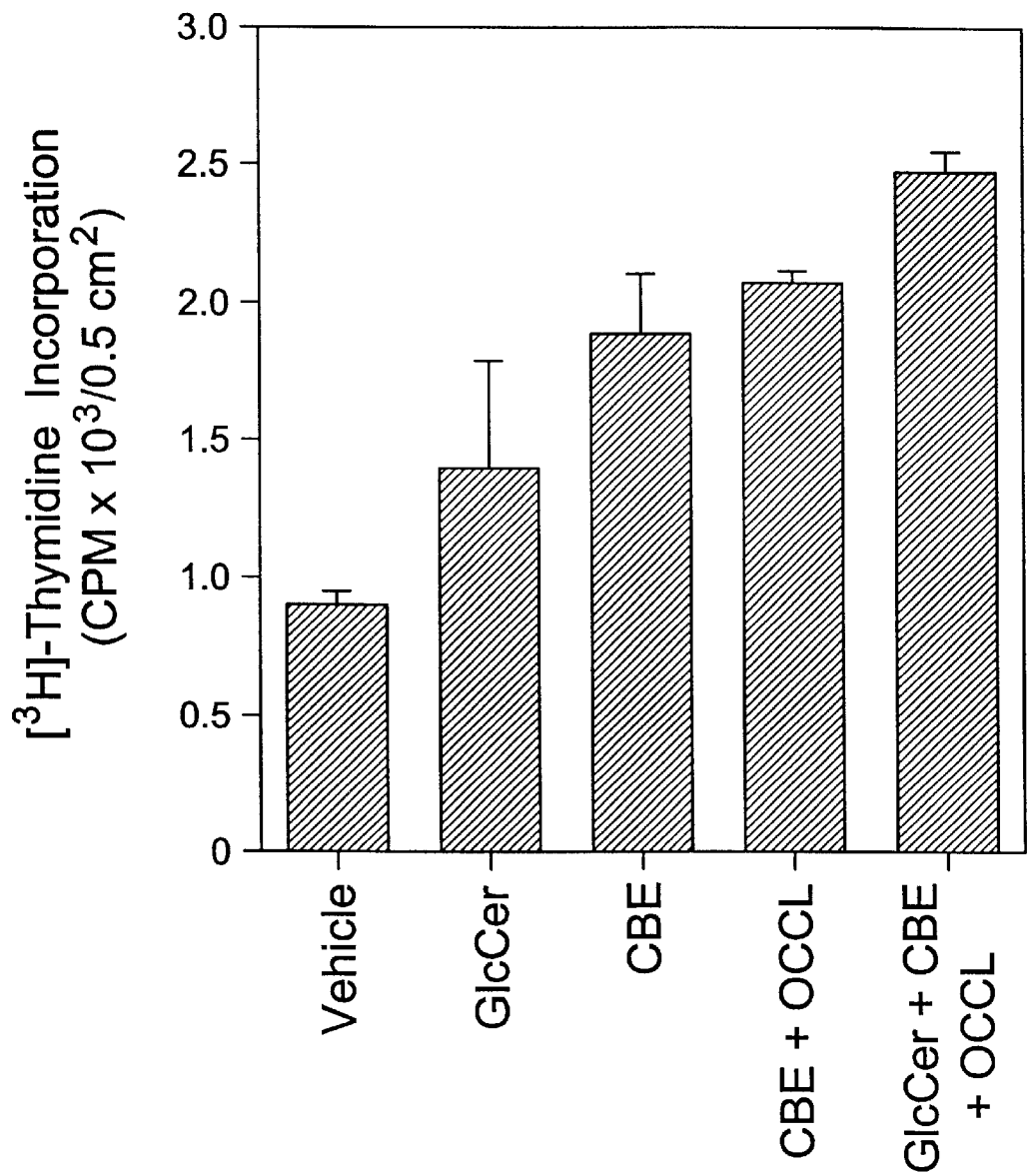

FIG. 27 compares the effect of glucosylceramide, ceramide and galactosylceramide on DNA synthesis in murine epidermis.

DESCRIPTION OF THE INVENTION

This invention is based on the demonstration by the applicants that the exposure of mammalian epithelial tissues to inhibitors of β-glucocerebrosidase resulted in improved skin thickness, smoothness, flexibility, and contour.

The inhibition of β-glucocerebrosidase, a central enzyme in glycosphingolipid metabolism (see FIG. 1), with a variety of specific and nonspecific agents resulted in a block of the metabolic production of ceramide from glucosylceramide. The inventors have shown that an increase in the glycosylceramide/ceramide balance results in multiple alterations in murine epithelium. Among these alterations is enhanced tissue growth (proliferation). Specifically, inhibitors of β-glucocerebrosidase administered alone or in conjunction with additional glucosylceramide, altered the balance of proliferation (growth) vs. differentiation in the target tissue. The inventors have demonstrated that inhibitors of β-glucocerebrosidase stimulated both the rate of DNA synthesis and the DNA content of mammalian skin. Moreover, the inventors showed that the balance of glucosylceramide to ceramide ratio is critical in the control of DNA synthesis.

In addition, the inventors have demonstrated that exogenously added glucosylceramide increased the rate of DNA synthesis and DNA content in cultured keratinocyte cells. When glucosylceramide was applied to murine skin in vivo, a similar increase in both DNA synthesis and DNA concentration was observed. Moreover the application of a related glycocerebroside, galactosylceramide, failed to stimulate the rate of DNA synthesis. The stimulation of cell proliferation thus appears to be specific for glucosyl moiety in glycocerebrosides. Furthermore, when β-glucocerebrosidase activity was blocked in skin and mucous membranes, accumulation of glucosylceramides was observed in the stratum corneum.

The application of conduritol B-epoxide (CBE) increased the thickness, firmness and pliability of murine skin. These changes brought about a marked alteration in appearance of the is skin with greater smoothness, decreased folding and wrinkling, improved resiliency and a generally healthier appearing skin.

The increase in glucosylceramide was accompanied by a depletion of extracellular ceramide. Normal levels of ceramide mediate epidermal permeability barrier function and prevent water loss (W. M. Holleran et al., J. Clin. Inv. 93:1756–1764 (1994). As a result β-glucocerebrosidase inhibitors produced a decrease in the permeability barrier and increased water loss (transepidermal water loss or TEWL).

Increased TEWL normally leads to desiccation of the stratum corneum through loss of water across the skin, as in the xerosis of aging and atropic dermatitis. The inventors have demonstrated in contrast that administration of these β-glucocerebrosidase inhibitors, with or without exogenous glycosylceramide, leads to increased moisturization and lubrication despite increased TEWL. This result can be attributed to the highly hygroscopic character of the increased glycosylceramide whether induced by the β-glucocerebrosidase inhibitors and/or form exogenous glycosylceramide.

The resultant increase in epithelial water content, along with the natural lubricating properties of excess glucosylceramide, markedly increased thickness of the stratum corneum, tissue strength, flexibility and resilience, and gave a smoother contour of the skin.

The inventors more specifically demonstrated that the application of β-glucocerebrosidase inhibitors increased both the rate of DNA synthesis and the total DNA content of epidermal and epithelial tissues. This increase took place among the proliferative basal cells of the epidermis, the layer of cells found juxtaposed with the dermis. As a result, the increased population of proliferative cells also enhanced the ability of skin to produce differentiated stratum corneum, resulting in thicker, more resilient skin.

The in vivo methods for stimulating epithelial proliferation and/or enhancing epithelial moisturization and lubrication will be useful to enhance the ability of skin layers to regenerate during wound healing after injury due to burns, physical trauma, and exposure to toxic agents, ultraviolet light and ionizing radiation. Hence the increased epithelial population and enhanced epithelial moisture/lubrication is effective to improve or restore the desired tissue continuity, strength, thickness, flexibility, texture, surface contour and cosmetic appearance.

The above methods will also be effective to treat, prevent, is or reverse the deterioration of epithelial tissues of aging, post-menopausal, or atrophic mucous membranes. The claimed method will also be effective in the treatment or prevention dry mucous membranes, including atrophic vulvar disease, dry mouth, dry eye and eye irritation syndromes (e.g., in smokers), and xerosis (dry skin) of dermatitic origin.

In another aspect of this invention the methods may be used to augment the growth of and expand selected tissue compartments of skin, accessory skin structures, such as nail and hair, mucous membranes, dermis and subcutaneous tissues. For example, expanded or thickened skin structures may be desired to cosmetically mask scarred or deficient dermal layers or subdermal structures. Examples include atrophic skin after incomplete wound healing, such as after cancer surgery, enhancement of skin and skin structures following cosmetic or therapeutic surgery of lips, palates, breasts and other organs, and aging skin, mucous membranes, hair, nails, and cutaneous glandular structures.

The compositions of the methods claiming glucocerebrosidase inhibitors and/or glycosphingolipid may also be applied to improve the appearance of skin for purely cosmetic purposes. For cosmetic purposes the composition of the invention herein is may be formulated to enhance the moisturizing and lubricating properties of cream, lotions, gels, or ointments.

The claimed methods may be used to decrease the effects of repetitive frictional abrasion, as for example, during athletic performance, for applications including hemorrhoidal suppositories, and for the treatment and prevention of all types of "dry eye" where insufficient glucosylceramide is present for normal moisturization and lubrication.

The composition of the method of this invention employs one or more inhibitors of β-glucocerebrosidase sufficient to provoke the above-described biochemical alterations to an extent required to cause enhanced tissue growth (proliferation) and/or stratum corneum moisturization/lubrication. A further enhancement of effectiveness can be expected if one or more of the inhibitors is co-administered with sufficient quantities of glucosylceramide or other glycosphingolipids.

The method of the invention may also be practiced with a composition comprising a glycosphingolipid. In a preferred embodiment of the method glucocerebroside is selected and applied.

In an additional embodiment of the invention is an in vitro method for stimulating proliferation and enhancing tissue moisturization and lubrication by administering to cells or tissues in culture an effective amount of a composition comprising a glycosphingolipid, one or more inhibitors of β-glucosidase or a combination of both the glycosphingolipid and the inhibitor. This method will be useful to stimulate epithelial cell proliferation in culture. The method will also permit the growth and increased moisturization/lubrication of organ cultured explants of skin and other epithelial tissues.

A "growth (proliferation)-stimulating and moisturizing/lubrication" amount means that the quantity of the inhibitor is sufficient to enhance the tissue proliferative rate so as to increase the population of epidermal cells resulting in an alteration of the texture of the epithelial layers, such as the stratum corneum or the keratinizing layer of mucous membrane. The absolute amount can vary according to the effectiveness of each inhibitor, the amount of co-administered glycosphingolipid, the frequency of administration, the subject age, and the tissue responsiveness of the subject. Most preferably the amounts should be determined by the affinity of the inhibitor for β-glucocerebrosidase and by the ability of the inhibitor, as well as co-administered glycosphingolipids, to reach the site of action in the target tissue.

As used herein, the term "subject" includes human and non-human mammals. Non-human mammals to which the claimed method may be applied include domesticated species such as dogs, cats, monkeys, cows, horses, llamas, sheep, pigs, and goats. Veterinary and commercial use of the method may also include any other mammals afflicted with skin wounds and cosmetic or other texture deficiencies.

The term "enhanced proliferation" as used herein relates to an increase in mass and/or cell population of the target tissue.

The term "enhanced moisturization/lubrication" refers to increased water and glycosylceramide content of mammalian epithelial tissues, resulting in altered texture of the epithelial layers, such as the stratum corneum or the keratinizing layer of mucous membranes as described above.

In a preferred method of the invention, one or more administrations of the composition will be by portal(s) deemed most effective for the condition treated. Thus, the composition of the method can be delivered to the target tissue by direct injection, oral, rectal, mucosal, opththalmic, corneal or conjunctival instillation, intravenous, is intraperitoneal, or intramuscular injection, or infusion after subcutaneous implantation.

In another preferred aspect of the method of the invention the composition can be delivered topically to the skin or mucosal surface, or instilled over the surface of any portion of the gastrointestinal, genitourinary, nasopharyngeal, auditory, or ocular mucosa. In other applications, the most efficacious route for a particular target tissue will be subcutaneous implantation of the composition of the method, providing for prolonged or gradual release.

The active substances will be provided to the subject in the composition in amounts sufficient to provide the desired physiological effect with no apparent toxicity to the host. In general, the inhibitor will be present in the composition in an amount of from about 0.0001% to about 20%, more preferably about 0.01% to about 5%, by weight of the total composition. The concentration of the co-administered glycosphingolipid can range from 0.0001% to about 60%, with the preferred range from 0.01% to 20% by weight of the total composition.

In a further embodiment of the invention the inhibitor(s) of the method can be applied singly or in combinations of inhibitors, alone or co-applied with glycosphingolipids to the skin or mucous membrane of a subject. Alternatively, they can be applied concurrently as separate formulations. Still further, one agent can be applied before, simultaneously with, or after applications of the other agent(s) provided that the time interval between the two (or more) is not too lengthy (e.g., typically, not more than about 24 hours).

Preferably and conveniently, the composition of the invention is administered to the target tissue in combination with a physiologically acceptable carrier. The carrier may comprise any conventional infusion or topical formulation base such as those described in Remington's "Pharmaceutical Sciences," 17th Edition (Mack Publishing Co., Pa.), the disclosure of which is incorporated by reference. For administering the composition of this invention, a lotion, solution, cream, ointment, paste, gel, suppository, aerosol, or nebulized formulation are representative of the topical compositions of this invention. Additional ingredients may be added to the topical composition, as long as they are physiologically acceptable and not deleterious to the epithelial cells and function. Such additives should not adversely affect either the enhanced tissue growth (proliferation) or moisturizing/lubrication properties of the above-noted enzyme inhibitors, nor cause the stability of the composition to deteriorate. Examples of ingredients which can be added to the compositions of the invention include stabilizers, oxidizing agents, reducing agents, preservatives, buffering agents, surfactants, emulsifiers, binding agents, fragrances, humectants, and the like so as to effectively retain the activity of the composition in a manner compatible with the route of administration.

Figure 1:
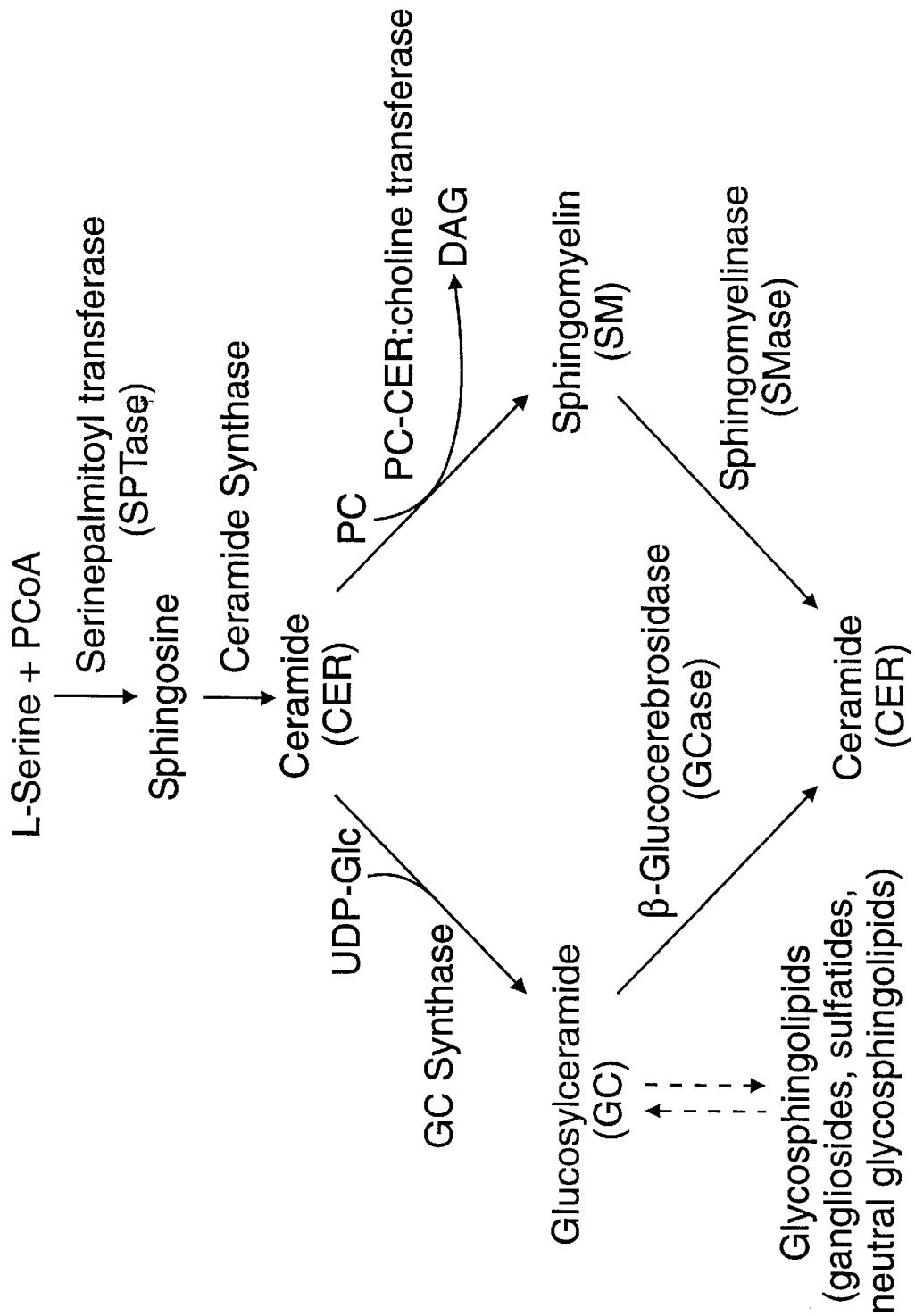
Figure 2:
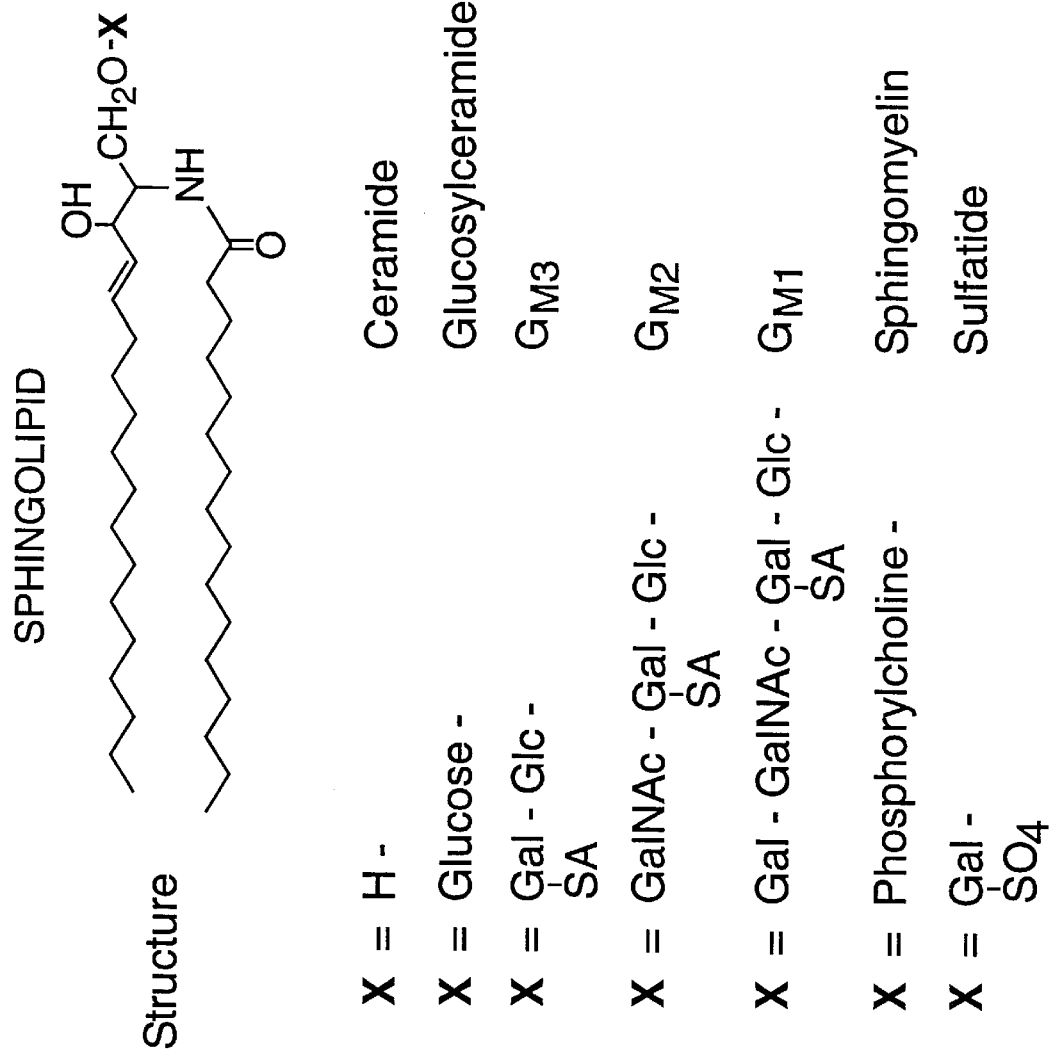
Figure 5:
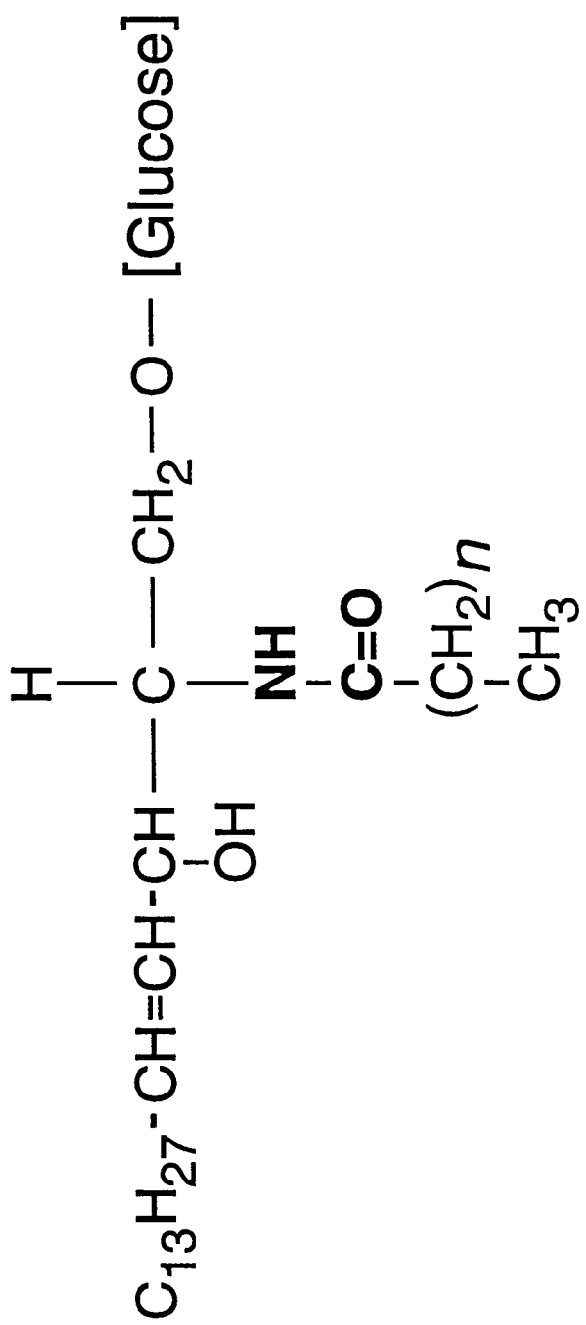

Other physiologically active agents may also be compounded with the composition of the method herein. These active agents may be included to ameliorate additional clinical complications of the treated condition. For example, antibacterial, antifungal and anti-inflamatory agents as well as analgesics may be added. Antibacterials may include erythromycin, bacitracin, polymyxin and mupriocin. Antifungal agents may include ketoconazole, clotrimazole, micronozole or amphotericin. Anti-inflamatory agents may include hydroxycortisone, desonide or other fluorinated or non-fluorinated steroidal agents. Analgesics may include camphor, phenol, menthol or pramoxime. β-glucosidase enzymes comprise a family of enzymes which hydrolyze glucose, specifically β-linked glucose, from either a protein or lipid core structure. In this enzyme family β-glucocerebrosidase specifically hydrolyzes β-glucose from glucosylceramide which has a ceramide core structure (c.f. FIGS. 1 & 5).

Inhibitors of the β-glucosidase family of enzymes also inhibit β-glucocerebrosidase in a specific or non-specific manner. However the effectiveness of the inhibitor depends primarily on the concentration of the inhibitor.

Thus inhibitors of glycosphingolipids-to-ceramide conversion include inhibitors of β-glucosidase, or more specifically, β-glucocerebrosidase, such as the conduritol group; e.g., bromoconduritol-B-epoxide, conduritol, cyclophellitol, bromoconduritol, conduritol-B-epoxide, and deoxynojirimycin, see FIG. 3 (Radin, N. S. and Vunnam, R. R., Methods in Enzymology (1981) 72:673–684).

Figure 4:
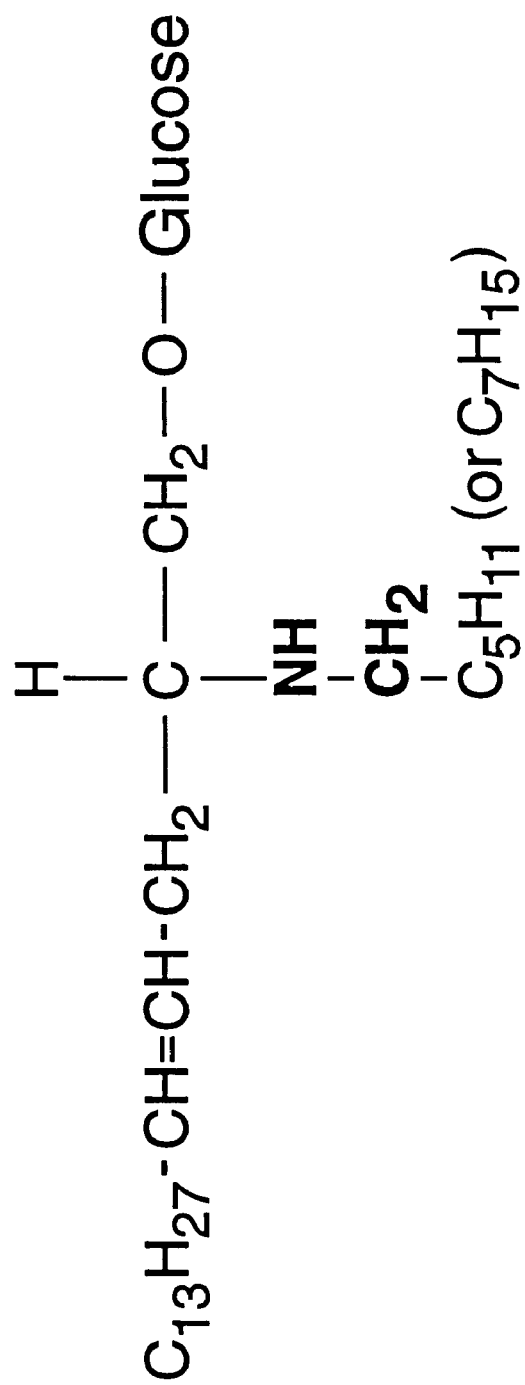

In addition, N-aglucosylsphingosine (sphingosine group varies from C14 to C22, with varying degrees of unsaturation and hydroxylation; acyl groups vary from C2 to C30) and related compounds are potent competitive inhibitors of β-glucocerebrosidase. The most effective acyl groups are the N-hexyl and N-octanoyl compounds, N-hexylglucosylsphingosine and N-octanoylglucosylsphingosine (Radin, N. S. et al., supra). These secondary amines eliminate the carbonyl (C=0) group from the N-acyl group on the ceramide backbone, substituting for the amide group (compare FIG. 4 with FIG. 5) in the normal ceramide backbone±glucose.

Figure 6:
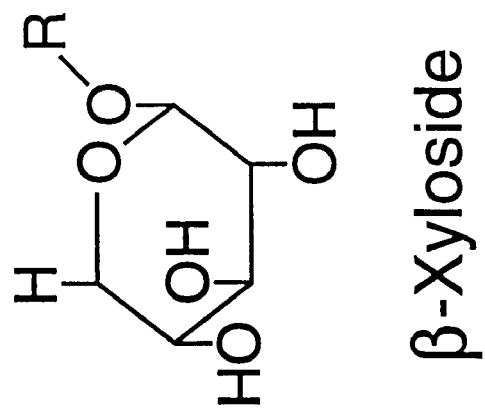

In addition, α- and β-xylosides of the structures shown in FIG. 6 are inhibitors of β-glucocerebrosidase.

Figure 7:
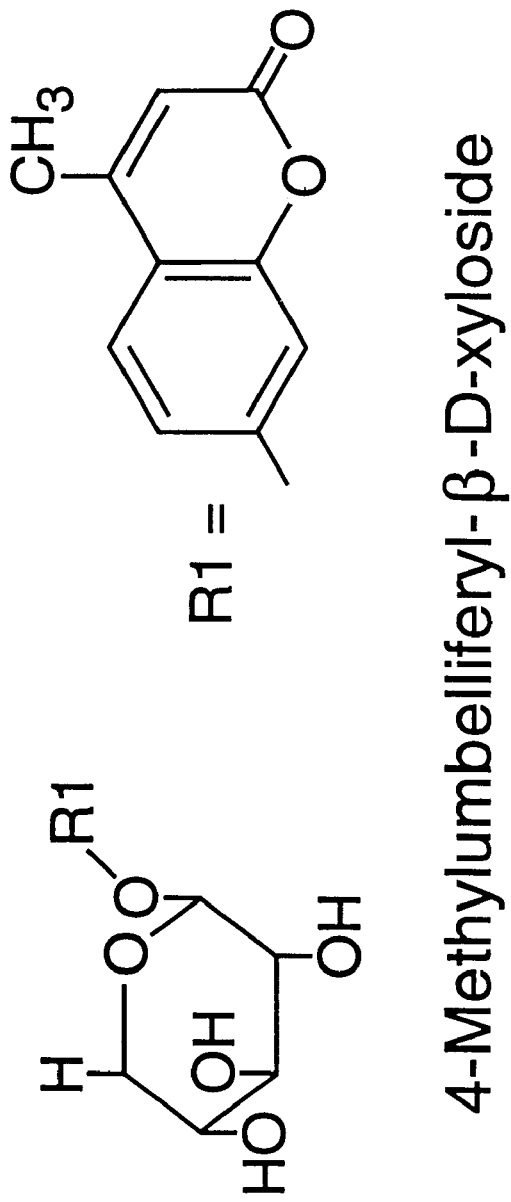

The most effective and preferred structures are esters of the β-xylosides, including the 4-methyl- and 4-methylumbelliferyl esters (FIG. 7). Other effective structures are p-naphthyl-β-xyloside, as well as both 4-methyl and 4-methylumbelliferyl-xyloside (Freeze, H. et al., J. Biol. Chem. 268:1618–1627 (1993).

An additional, miscellaneous group of β-glucosidase inhibitors are effective inhibitors of β-glucocerebrosidase (Ermert, P. et al., Carbohydrate Res. 250:113–128, 1993). The most effective of these are the four molecules shown in FIG. 8, as well as their esters and analogues. Of these four base structures, the D-glucono-1,5-lactone is the most specific for β-glucocerebrosidase (Weeley, et al., Biochem. Biophys. Acta 1181:55–62,1 1993).

While the present invention has been described with respect to preferred embodiments thereof, it will be understood that various changes and modifications will be apparent to those skilled in the art and that it is intended that the invention encompass such changes and modifications as falling within the scope of the appended claims. The following non-limiting examples are provided to further illustrate the present invention.

EXAMPLE 1
Preparation of Conduritol Gel.

The following ingredients were combined and blended uniformly together to produce a gel formulation:

| Ingredients | Percent by Weight |
| --- | --- |
| Conduritol | 2.0 |
| Bovine cerebroside (monohexylceramides) | 2.0 |
| Carboxyvinyl polymer 940 | 1.0 |
| Ethanol | 30.0 |
| Propylene glycol | 30.0 |
| Triethylamine | 1.5 |
| Distilled water | Remaining part |

A solution was prepared by mixing all the ingredients except triethylamine. Neutralization of the aqueous solution with triethylamine furnished a viscous gel. Conduritol was obtained from Toronto Research Chemicals (Toronto, Canada).

EXAMPLE 2
Preparation of Bromoconduritol-B-epoxide Ointment.

The following ingredients were combined and blended uniformly together to produce an ointment formulation:

| Ingredients | Percent by Weight |
| --- | --- |
| Bromoconduritol-B-epoxide | 1.0 |
| Monohexylceramide (cerebroside) | 2.5 |
| Aquitane base (mineral oil 95%, polyethylene 5%) | Remaining part |

Blends of the active ingredients in ointment base were mixed together for 30 minutes at 40 rpm followed by 60 minutes at 25 rpm under vacuum to prevent aeration. Aquitane base is available from Lederle Laboratories ( ), Bromoconduritol-B-epoxide was synthesized as described by Legler. (Legler, G., 46:368–381, in *Methods in Enzymology* (1988), W. B. Jacoby and M. Wilchek, editors, Academic Press, Inc., New York, N.Y.)

EXAMPLE 3
Preparation of Cyclophellitol Gel.

The following ingredients were combined and blended uniformly together to produce a cream formulation:

| Ingredients | Percent by Weight |
| --- | --- |
| Cyclophellitol | 1.0 |
| N-hexylglucosylsphingosine | 2.0 |
| Monoloxylceramides | 2.0 |
| Cetyl/stearyl alcohol | 25.0 |
| Glycerin | 5.0 |
| Oleic acid oleyl ester | 3.0 |
| Distilled water | Remaining part |

Cetyl/stearyl alcohol (25 g), 10 g of an aqueous suspension of the active ingredient and 3 g of oleic acid oleyl ester were heated to 80° C. and emulsified by stirring at that temperature with a mixture of 5 g of glycerin and 57 ml of water.

EXAMPLE 4
Preparation of β-Xyloside Gel.

The following ingredients were combined and blended uniformly together to produce a cream formulation:

| Ingredients | Percent by Weight |
| --- | --- |
| β-xyloside | 2.5 |
| Monohexylceramide (cerebrosides) | 2.0 |
| Cetyl/stearyl alcohol | 40.0 |
| Polysorbate 80 | 10.0 |
| Distilled water | Remaining part |

β-D-xyloside was obtained from Sigma Chemical Co. (St. Louis, Mo.)

EXAMPLE 5
Effect of Glucosylceramide on Growth of Cultured Human Keratinocytes.

To determine the ability of exogenous glucosylceramides (GlcCER) to stimulate epidermal proliferation, we applied various concentrations of GlcCER to cultural human keratinocytes (third passage). Keratinocytes were isolated from human neonatal foreskins by a modification of the method of Pittelkow, M. R. and Scott, R. E. ((1986) Proc. Mayo Clin. 61:771–777) Cells were added to 100 mm plastic Petri dishes at a density of 1 to $2 \times 10^4$ cells/cm$^2$, and grown initially in 10 mls of Keratinocyte Growth Medium (KGM) (Clonetics, San Diego, Calif.) with 0.07 mM calcium. The cultures were maintained at 35° C. under 5% $CO_2$ in air, with medium changes performed three times weekly. After the cells reached 70%–80% confluence, they were switched to KGM medium containing 1.2 mM calcium, and harvested at one week post-confluence. GlcCER was added for the last 24 hours of culture and $^3$H-thymidine (1 μCi/ml) was added one-to-three hours prior to harvesting of cells for measurement of DNA synthesis and DNA content. (Proksch, E., et al., J. Clin. Invest. 87:1668–1673 (1991).

In three separate experiments (Table 1), we showed an increased proliferation over controls, with a maximum effect observed at 1.25 μM. No further increase was observed at 5 μM concentrations. These results show that exogenous GlcCER causes a significant increase in keratinocyte proliferation.

TABLE 1

Effect of Exogenous Glucoceramide on Keratinocyte Proliferation.

| Expt # | GlcCER Conc. (μM) | DNA Content (% of Control) | $^3$H]-Thym. Incorporation (% of control) |
| --- | --- | --- | --- |
| #1 | 1.25 | 124 ± 2 | 118 ± 0.5* |
| #2 | 1.25 | 111 ± 6 | 117 ± 2.0* |

NHK cells were treated with glucosylceramide for 24 hours. (n = 6 ± S.E., *p < 0.001 vs. control)

EXAMPLE 6
Glucosylceramide Overrides the Inhibitory Effects of Ceramide.

Using the method described in Example 5, incorporation of [$^3$H]-thymidine and total DNA content were measured in cultured human keratinocytes (CHK) grown in serum-free keratinocyte growth medium (KGM) supplemented with 0.07 mM calcium. Cultured cell were further supplemented as indicated, with ceramide (Cer; 5 or 10 μM), glucosylceramide (GlcCER; 1.25or 2.5 μM), or a combination of ceramide and glucosylceramide (10 and 1.25 μM, respectively).

Figure 9:
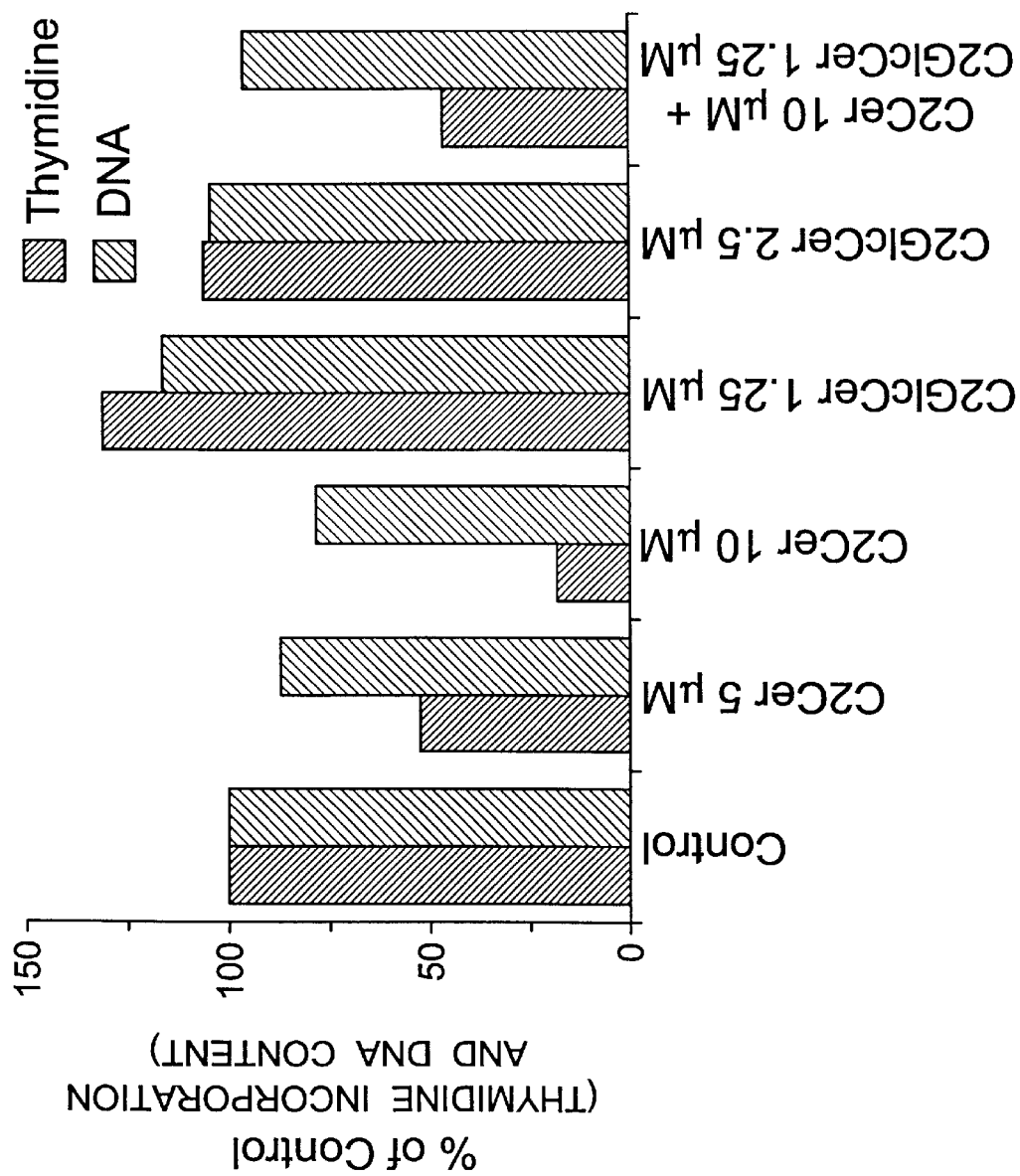
FIG. 9 shows the effect of glucosylceramide and ceramide on DNA synthesis in keratinocytes.

After 24 hours of treatment, ceramide inhibited thymidine incorporation with a corresponding decrease in DNA content (FIG. 9), while glucosylceramide (1.25 µM) increased both thymidine incorporation and DNA content. Co-administration of glycosylceramide with ceramide blocked the inhibitory effect of ceramide, increasing thymidine incorporation by approximately 2-fold over ceramide alone. Values represent the percent increase vs. unsupplemented control for six separate determinations. These data suggest that glucosylceramide and ceramide have coordinate regulatory effects on keratinocyte proliferation.

EXAMPLE 7
Increasing Glucosylceramide Concentration Alters Ceramide Inhibition of CHK Proliferation.

CHK cells were grown in serum-free KGM supplemented both with 0.07 mM calcium and 10 µM ceramide (CER). Increasing concentrations of glucosylceramide were added (2.5 to 10 µM), and both [$^3$H]-thymidine (1 µCi/ml) and [$^{14}$C]-leucine (1 µCi/ml) incorporation assays were performed.

Figure 10:
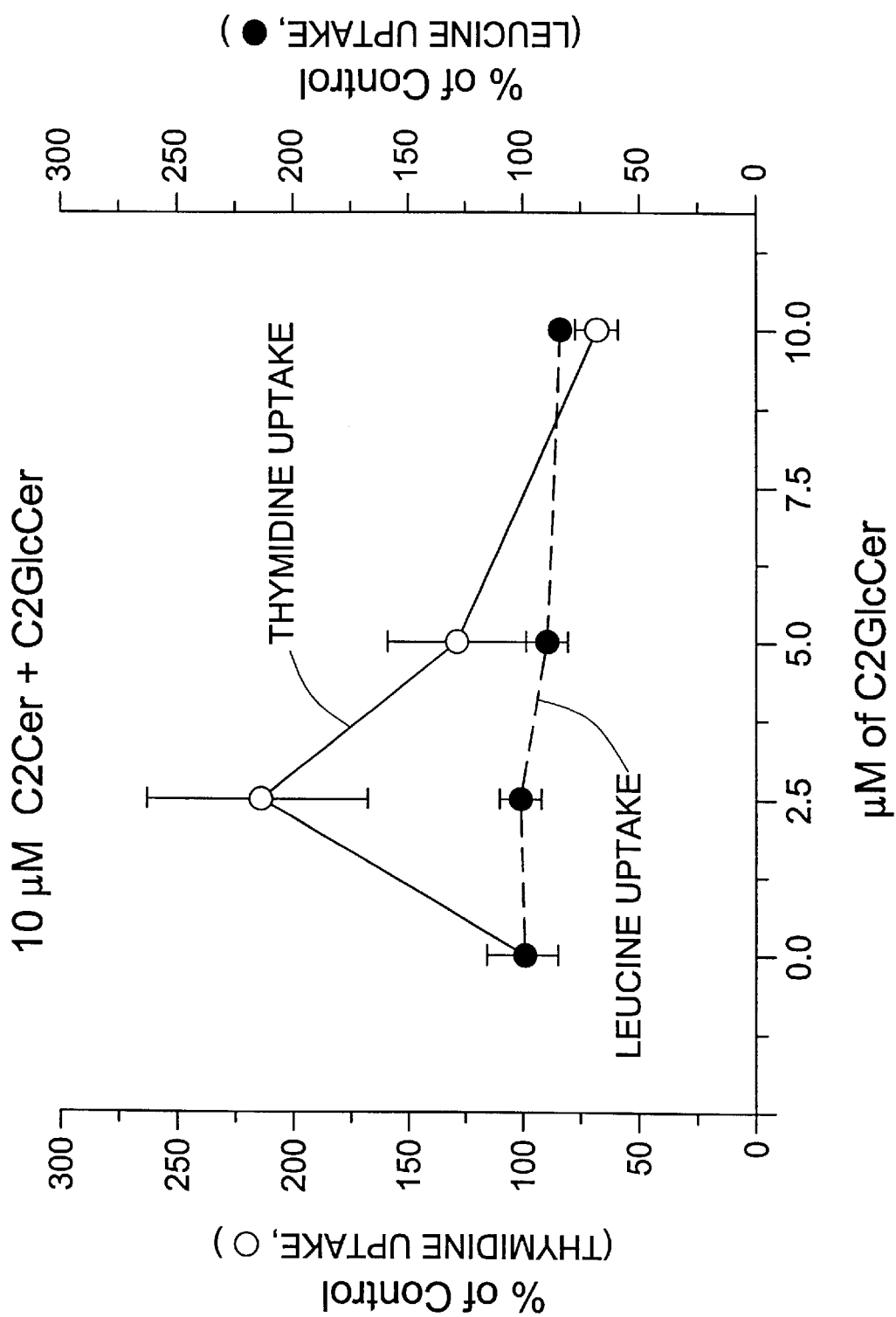
FIG. 10 shows that increasing glucosylceramide concentration overcomes the ceramide inhibition of CHK proliferation.

Low concentrations of glucosylceramide (2.5 and 5.0 µM) stimulated thymidine incorporation (open circles) relative to ceramide-containing control, while leucine incorporation (closed circles) was not altered (FIG. 10). Higher glucosylceramide concentrations (10 µM) did not override the ceramide effect, likely due to hydrolysis back to free ceramide. Values represent the mean (±SD) for n≥3.

EXAMPLE 8
Effect of Increasing Ceramide and Glucosylceramide Concentrations on Keratinocyte Proliferation.

Figure 11:
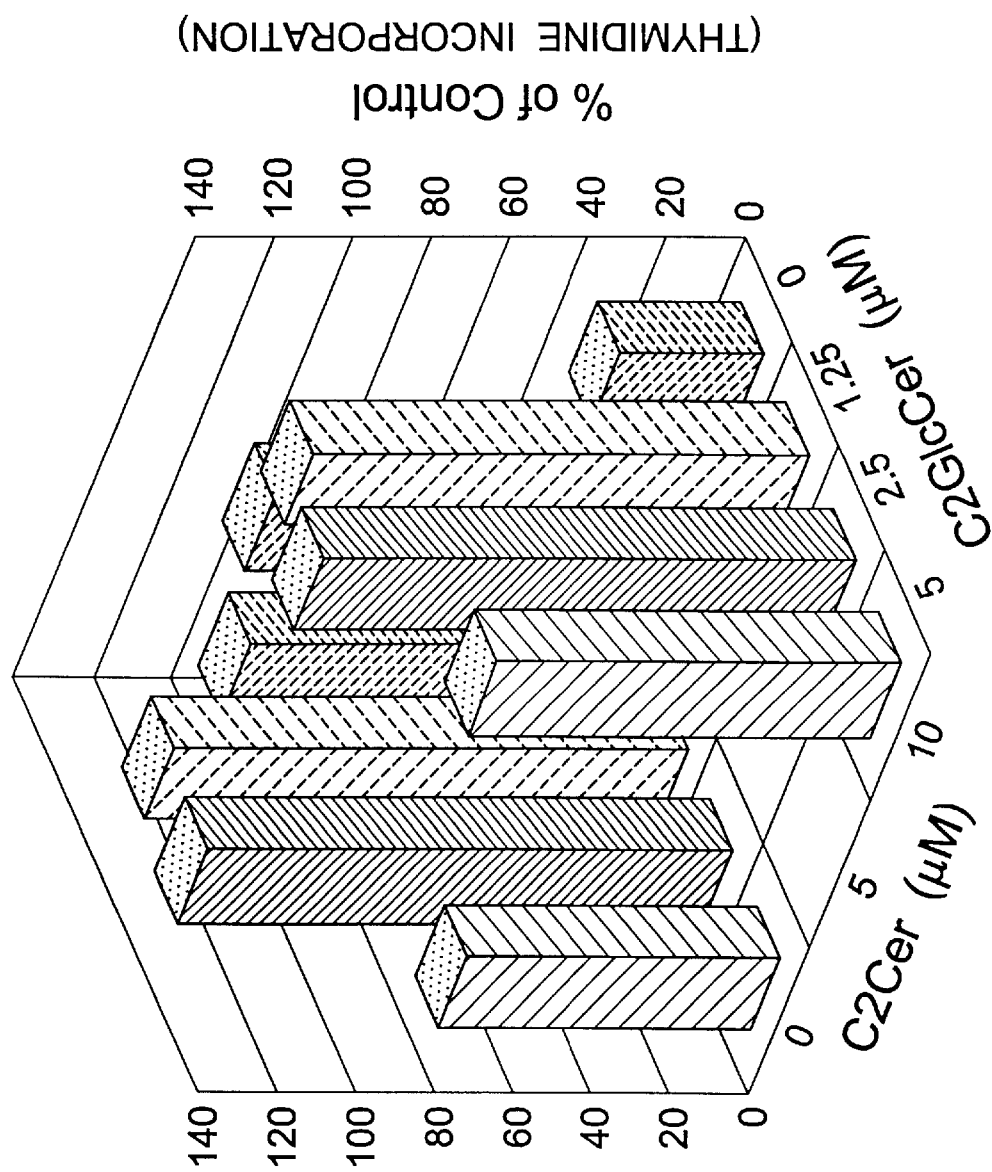
FIG. 11 shows the effect of increasing ceramide and glucosylceramide concentrations on keratinocyte proliferation.

In another set of experiments (FIG. 11) we showed directly not only the stimulatory effect of exogenous glucosylceramide (GlcCER) on human keratinocyte proliferation, but also the antagonistic relationship between GlcCER and exogenous ceramides (CER).

CHK cells were grown (as in Example 6) in serum-free KGM (0.07 mM calcium) and supplemented with increasing concentrations of ceramide (CER) alone (dark bars), glucosylceramide (GlcCer) alone (back row), or the combination of ceramide (10 µM) with increasing glucosylceramide (front row). Ceramide alone was again inhibitory, as 10 µM resulted in approximately 65% inhibition of [$^3$H]-thymidine incorporation (35% of control). Glucosylceramide alone again stimulated thymidine incorporation (>20%) at low concentrations (1.25 and 2.5 µM). The inhibitory effect of ceramide was reversed by glucosylceramide coadministration (front row; compare 0 vs. 1.25 µM GlcCER).

When GlcCER concentrations were increased to 1.25 and 2.5 µM, we again observed a significant stimulation of DNA synthesis (methods same as in prior example). However, at higher concentrations of GlcCER proliferation rates decreased due to the transformation of GlcCER to CER (by β-GlcCERase). These studies demonstrate that GlcCER alone causes only a modest increase in proliferation, because above a threshold concentration, it begins to be metabolized into CER (Example 9). These results prompted the application of β-glucocerebrosidase inhibitors alone, or in conjunction with GlcCER to further stimulate cellular proliferation.

EXAMPLE 9
Inhibitory Effects of Higher Glucosylceramide Concentrations are Due to Ceramide Formation.

Figure 12:
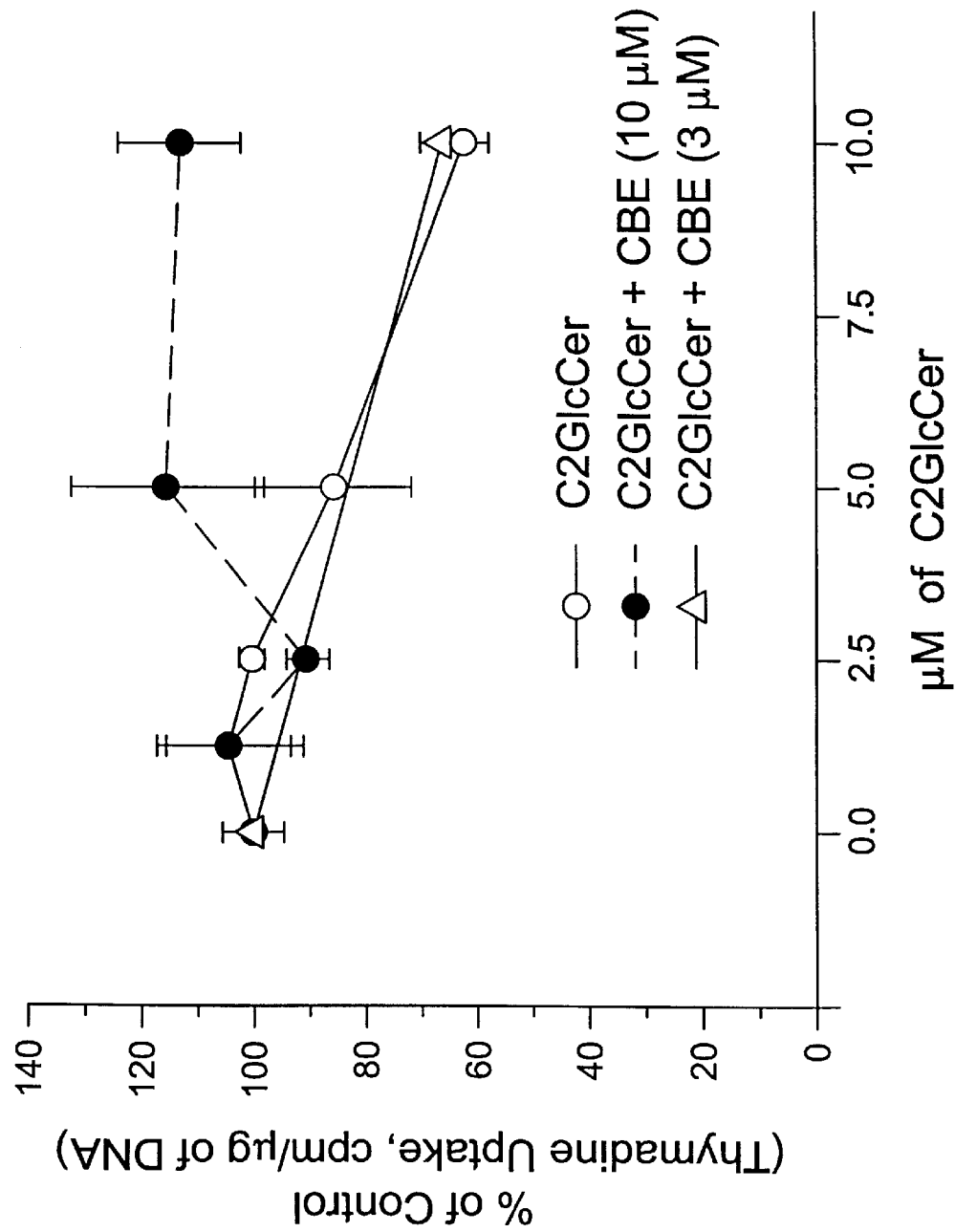
FIG. 12 shows that the inhibitory effects of higher glucosylceramide concentrations are due to ceramide formation.

CHK cells were grown (as in Example 6) in serum-free KGM (0.07 mM) supplemented with glucosylceramide (GlcCER) alone, or in combination with the β-glucocerebrosidase-inhibitor, CBE (3 or 10 µM) (FIG. 12) Incorporation of [$^3$H]-thymidine was measured at 24 hours following supplementation, and values are reported as percent of unsupplemented controls (mean ±S. D.; n>6). Addition of CBE (10 µM; closed circles) blocked the inhibition of thymidine incorporation caused by higher glucosylceramide concentrations (open circles). A low CBE concentration (3 µM) was ineffective. These data demonstrate that hydrolysis of glucosylceramide to ceramide is responsible for the observed inhibitory effects occurring at higher glucosylceramide concentrations.

EXAMPLE 10
Effect of Bromoconduritol-B-epoxide on Transepidermal Water Loss.

To determine whether inhibitors of β-glucocerebrosidase would cause more profound effects than applications of exogenous GlcCER alone (examples 5&6), we next applied the specific, suicide inhibitor, bromoconduritol-B-epoxide (BrCBE) to intact hairless mouse skin (Simonsen Laboratories, Gilroy, Calif.) (Holleran, W. M. et al., J. Clin. Invest. (1993) 91:1656–1664). BrCBE (325 nmol in 20 µl propylene glycol:ethanol, 7:3 vols) was applied once daily for 0–14 days. (Holleran, W. M. et al. (1994) J. Clin. Inv. 93:1756–1764)

Transepidermal Water Loss was determined by using a MEECO electrolytic water analyzer (MEECO, Warrington, Pa.). Water loss measurements are recorded over a small area of skin (0.5 cm$^2$) in parts per million/0.5 cm$^2$ per hour over background.

Figure 13:
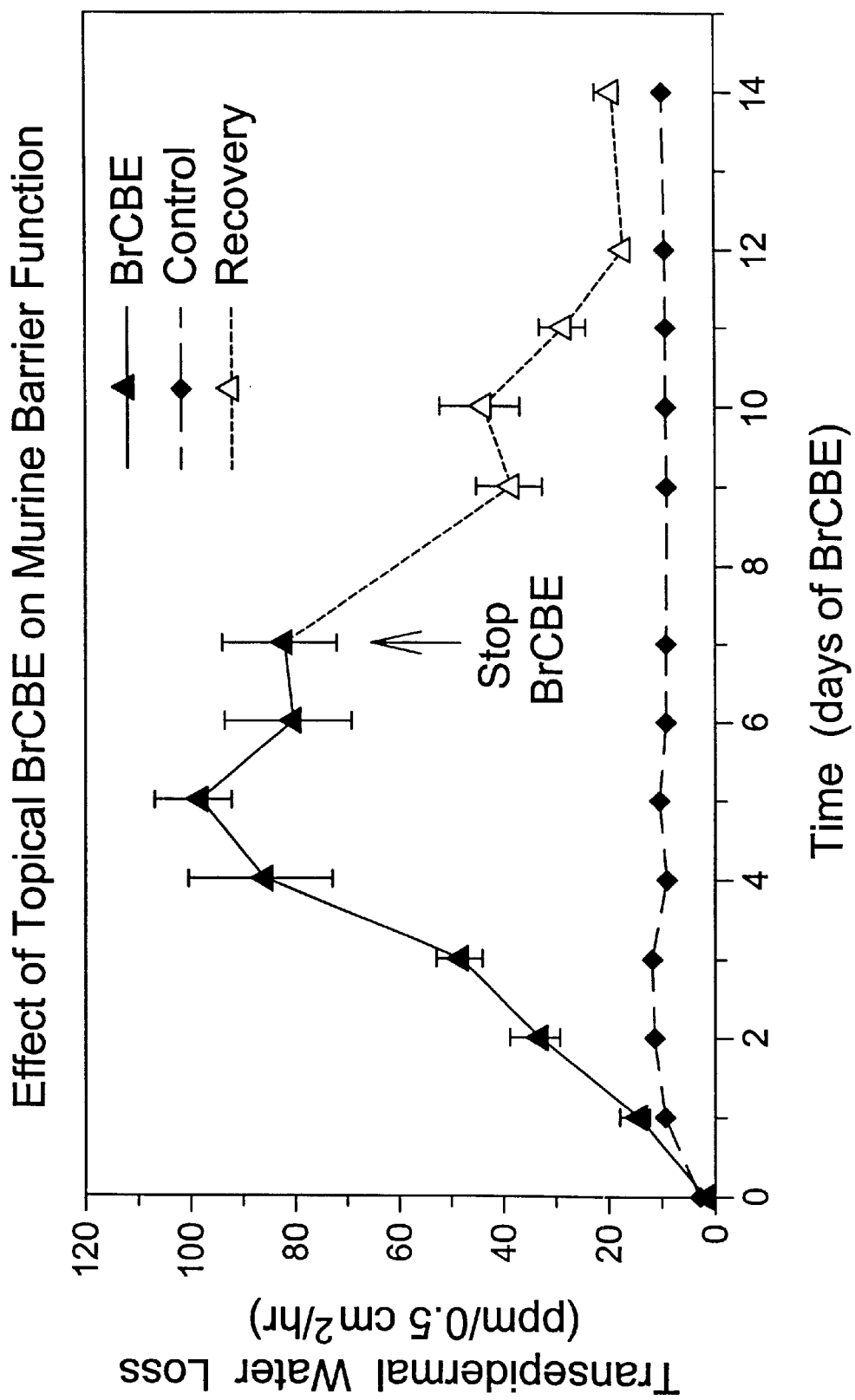
FIG. 13 shows the effect of topical BrCBE on murine barrier function.

BrCBE (FIG. 13) caused a progressive defect in permeability barrier function, which plateaued after the four daily application at levels about 10–15 times normal. Moreover, epidermal β-glucocerebrosidase activity was reduced by about 95% (5% of normal). Similar changes in TEWL occurred with topical applications of two other β-glucocerebrosidase inhibitors, one chemically related to BrCBE and the other unrelated (see examples below). These data showed that topical inhibitors of β-glucocerebrosidase cause a progressive, but limited loss of permeability barrier integrity, accompanied by changes in skin moisture content and texture.

This increase in TEWL was accompanied by a marked increase in skin smoothness and softening of the BrCBE-treated skin surface, as well as increased moisture content. BrCBE-treated skin, when compared to vehicle-treated skin, showed a reduction of normal skin wrinkling. Skin wrinkling was reduced (i.e., less apparent to visual inspection) with no indication of inflammation or edema. BrCBE-treated skin also showed similar decrease in wrinkling relative to the adjacent untreated skin.

EXAMPLE 11
Determination of Epidermal Lipid Content with BrCBE Treatment.

Hairless mice were treated with BrCBE for 5 days as described in Example 10. The following high performance thin layer chromatograph (HPTLC) system was developed for optimal separation of ceramides and glucosylceramides for quantitation by spectrodensitometry. Extracts were applied to precleaned 10×20 cm HPTLC plates, 0.5 cm from lower edge of the plate and fractionated sequentially in a horizontal developmental chamber (Camag, Muttenz, Switzerland) in the following solvent systems: 1) chloroform:methanol:acetic acid (190:9:1), v/v/v) to the top, twice; 2) chloroform:methanol:acetone (76:20:4, by volume) to 30 mm. Between each development, the plate was dried for 5 minutes on a hot plate (40° C.), cooled for 2 minutes, and equilibrated in the tank with the solvents for 3 minutes. After final development, the plates were dried, cooled, dipped in charring solution (1.5% cupric sulfate in acetic acid: sulfuric acid:orthophosphoric acid:water (50:10:10:30, by volume) for 15 seconds, dried (40° C.) for 5 minutes, and then charred at 180° C. for 15 minutes. Plates were scanned with a variable wavelength scanning densitometer (Camag, Muttenz, Switzerland). Lipid amounts for each fraction were estimated using ceramides 3 and 4, and galactosylceramides 1 and 2 as reference standards (Sigma Chemical Co., St. Louis, Mo.).

Figure 14:
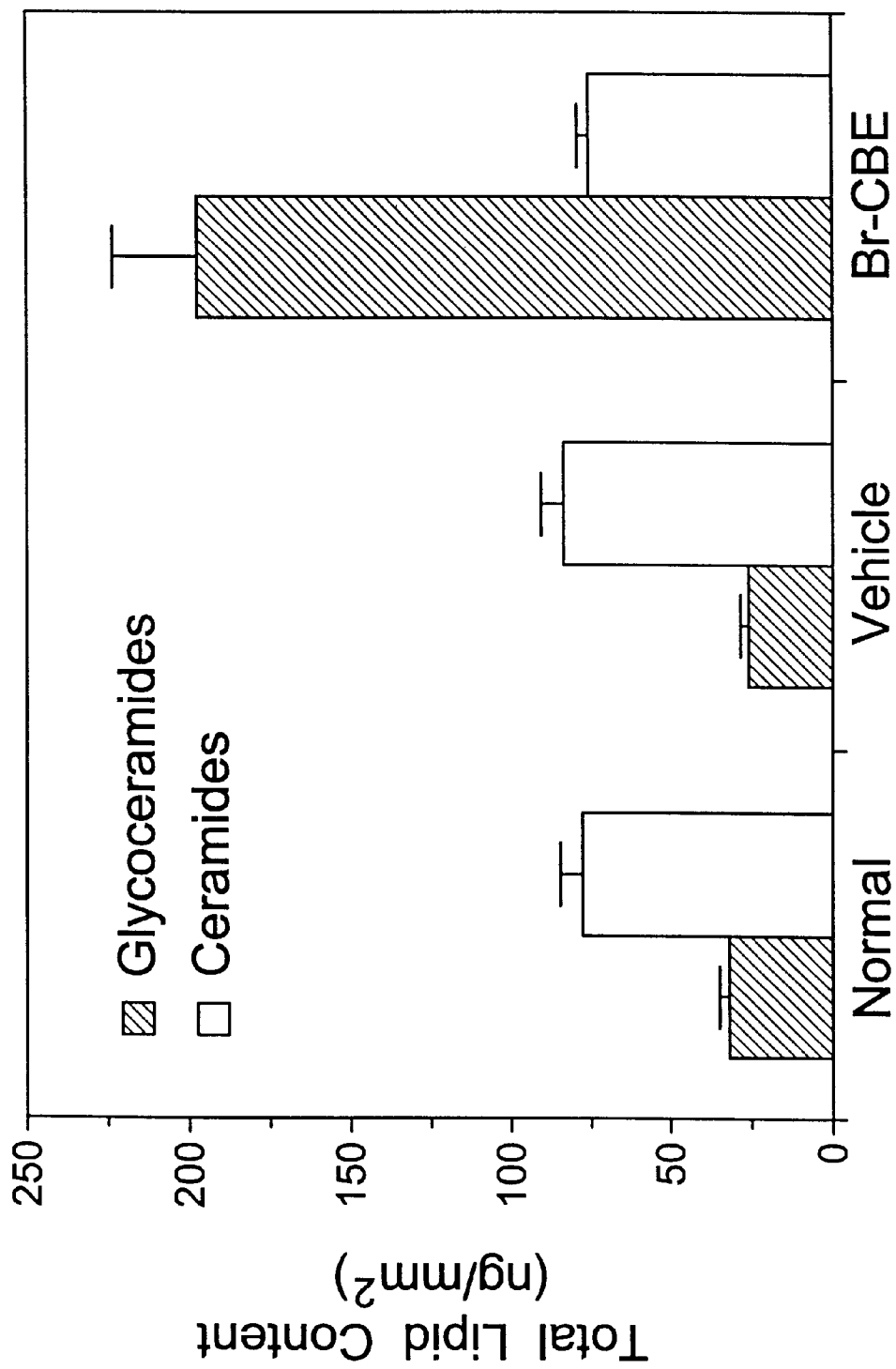
FIG. 14 shows that permeability barrier disruption is accompanied by an accumulation of glucosylceramides.

The lipid content of BrCBE-treated hairless mouse stratum corneum is shown in FIG. 14. BrCBE-treated mice showed an eight to ten-fold increase in stratum corneum glucosylceramides over vehicle-treated and/or untreated murine stratum corneum. The results showed that the biochemical abnormality leading to permeability barrier disruption is an accumulation of glucosylceramides (rather than loss of ceramides).

EXAMPLE 12
Histology of BrCBE-treated Murine Epidermis.

Skin from BrCBE and control treated mice were prepared as described previously (Holleran, W. M. et al. (1993) 91:1656–1664) The epidermis of a hairless mouse was treated with the β-glucocerebrosidase inhibitor, BrCBE (325 nmol/5 $cm^2$/day), or a vehicle control, for five consecutive days. Skin biopsies were obtained, and paraffin-sections were stained with hematoxylin and eosin (H&E).

Figure 15A:
FIG. 15 shows the histology of BrCBE-treated and vehicle-(i.e., control) treated murine epidermis.
Figure 15B:
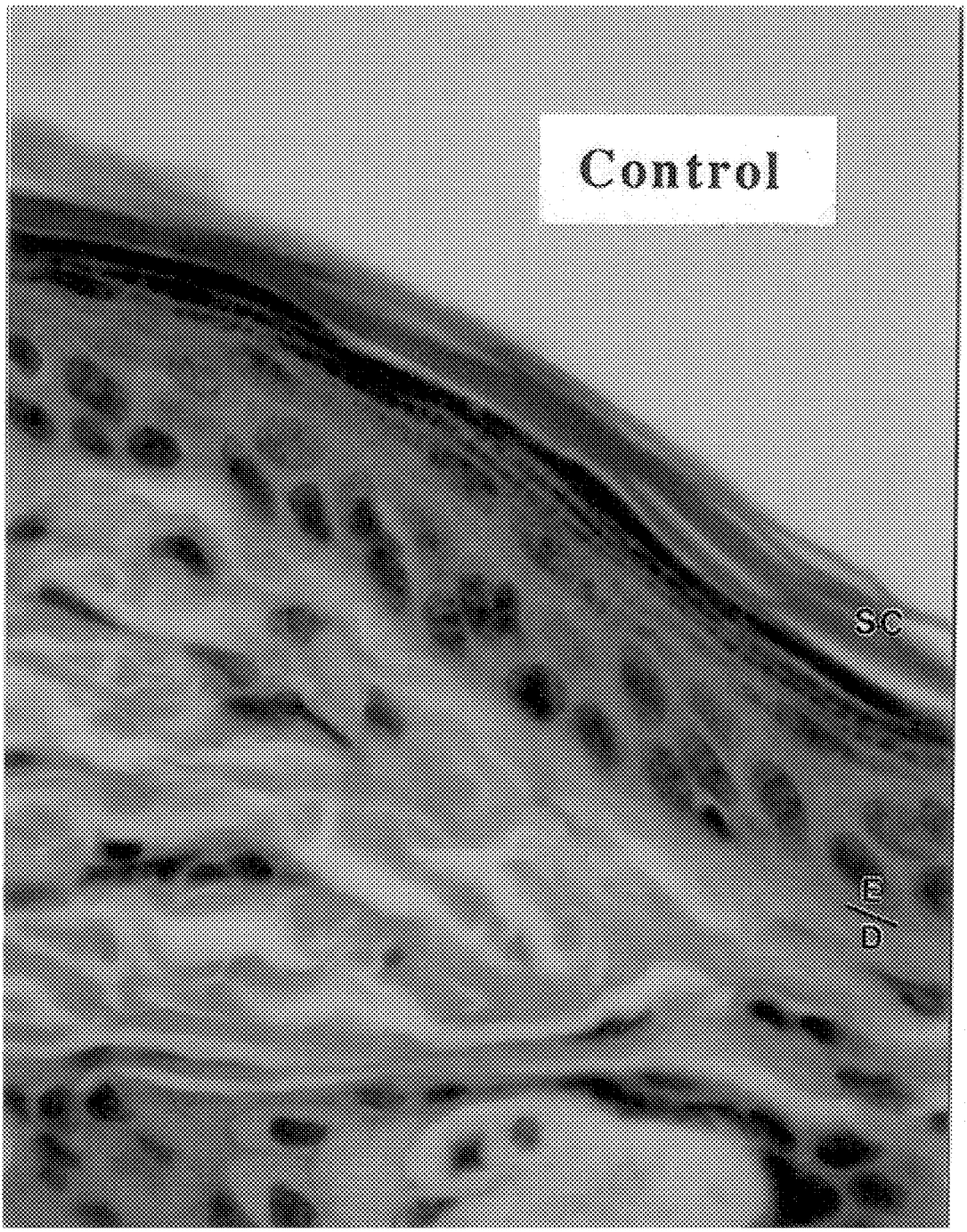

BrCBE treatment results in a thickened epidermis in comparison to vehicle-treated controls (FIG. 15, SC=stratum corneum, E/D=epidermis/dermis This thickening can be attributed to epidermal hyperproliferation (see data on epidermal DNA synthesis and DNA content in later examples).

BrCBE-treatment resulted in a substantial (1.5 to 2-fold) increase in epidermal thickness, the result of increased keratinocyte proliferation. Lipid extracts from whole epidermis of animals treated in parallel revealed increased epidermal glucosylceramides, with a decrease in ceramide content (see examples below).

EXAMPLE 13
Electron Microscopy of BrCBE-treated Mouse Skin.

Hairless mice were treated with BrCBE as described in Example 10. Tissue samples from hairless mouse skin were fixed first in glutaraldehyde and then post-fixed in 0.2% ruthenium tetroxide prior to plastic embedding, ultrathin sectioning, and examination in a Zeiss 10A electron microscope (Hou et al. (1991) J. Invest. Dermatol. 96:215–223).

Figure 16A:
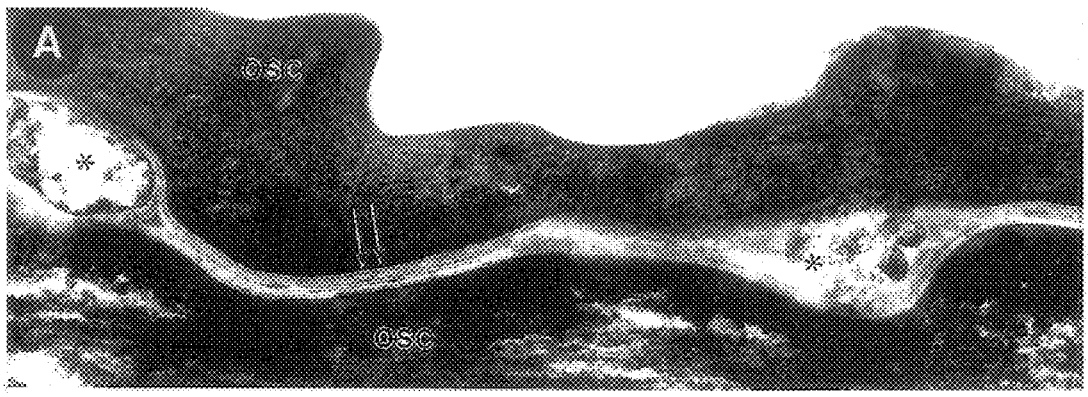
FIG. 16 shows ultrastructure of BrCBE-treated murine epidermis.
Figure 16B:
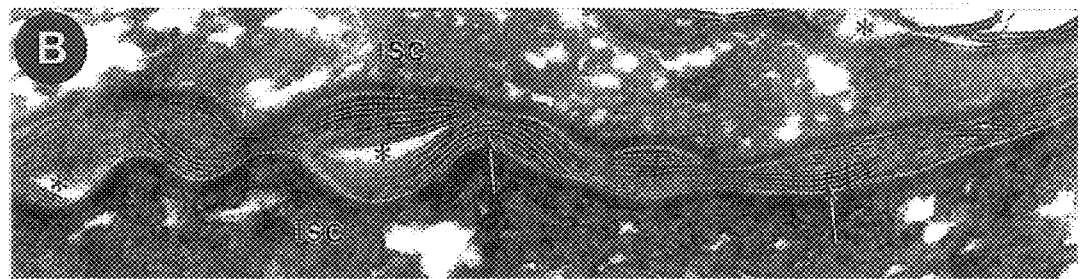
Figure 16C:
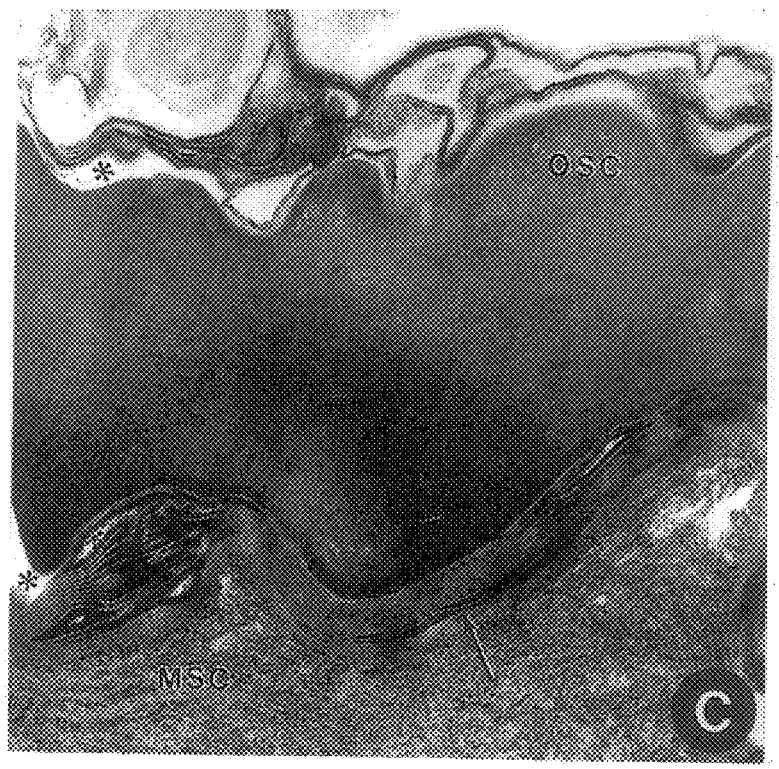
Figure 16D:
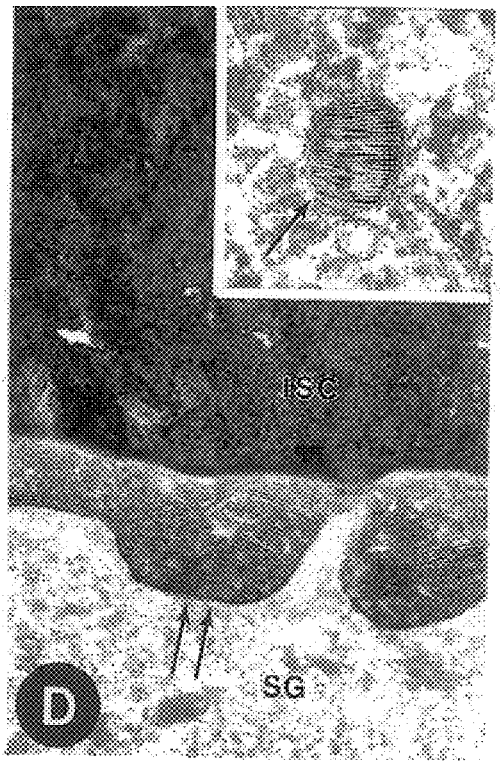

BrCBE causes abnormal (immature) membrane structures to appear in the stratum corneum intercellular spaces (FIGS. 16B–C, see arrows; FIGS. 16A–D, OSC=Outer stratum corneum, ISC=Inner stratum corneum, MSC=mid stratum corneum, SG=stratum granulosum.) However lamellar bodies, which are found at the base of the stratum corneum and secrete glucosylceramides, appear completely normal (FIG. 16D, see arrows).

FIGS. 16A shows normal structures in vehicle-treated control samples. These results show that BrCBE-inhibition of β-glucocerebrosidase results in abnormal stratum corneum membrane structures. This abnormality can be attributed to the accumulation of glucosylceramides, which lead to enhanced moisture content and altered surface texture.

EXAMPLE 14
Effect of Conduritol-B-epoxide in Epidermal DNA Synthesis.

To assess the effects of a topical β-glucocerebrosidase inhibitor, conduritol-B-epoxide (CBE) in epidermal DNA synthesis two slightly different dosage protocols have been employed. In all cases, mice were treated topically with 20 µl to 40 µl of 250 nmol/µl CBE bid for 2–5 days on the right flank. On the last day, the mice were injected intraperitoneally with $^3$H-thymidine (1 µCi/G body weighty diluted 1:10 in 100–200µl isotonic NaCl. After one hour the mice were sacrificed. Whole skin was excised and subcutaneous fascia and fat were is removed by scraped. Skin samples were placed dermis side downward onto 10 mM EDTA in phosphate buffered saline (PBS-CMF; pH 7.4) and incubated at 37° C. for 40 min The skin was blotted dry with a tissue and epidermis removed by scraping with a surgical blade. The epidermis was minced into small pieces and placed in microcentrifuge vials. Samples were immediately snap frozen and stored in liquid nitrogen until immediately prior to preparation of the epidermal homogenates. 300 µl of 10 mM EDTA in PBS-CMF (pH 7.4) was added to all samples which then underwent tissue homogenization using Polytron (15 sec, ×2 on ice. Polytron tip was rinsed between each homogenization with 400 µl 10 mM EDTA in PBS-CMF. Rinses were combined with same original samples. Samples were sonicated twice for 10 sec on ice. 100 µl of 20% TCA was added and left for 10 min at 4° C. Samples were centrifuged at 2000×g at 4° C. for 5 min. The supernatant was discarded. 500 µl of 5% TCA was added and the samples were centrifuged at 2000×g at 4° C. for 5min. The supernatant was discarded and this step was repeated again. The precipitate was resuspended in 1 ml of 1N NaOH and vortexed. 400 µl or NaOH plus 400 µl of 1N HCl with 8 ml Ecolume was used as a background blank. Vials were counted the following day.

FIG. 17 shows the incorporation of $^3$H-thymidine in the epidermis of hairless mice treated for five days with the β-glucocerebrosidase inhibitor, CBE (750 nmol/5 $cm^2$/day), or with a vehicle control. Incorporation of [$^3$H]-thymidine was measured after intra-peritoneal injection as described above. Values represent the average of two separate measurements on each of three CBE-treated and vehicle-treated animals. These data demonstrate an increased proliferative index (approximately 1.6) for CBE-treated epidermis over control epidermis.

EXAMPLE 15
Increases in DNA Content in CBE-treated Mice.

In addition to measuring DNA synthesis by [$^3$H]-thymidine incorporation, total epidermal DNA content was determined after applications of CBE. 100 µl of epidermal homogenate was obtained from mice and stored at −70° C. Samples were diluted with Hoechst buffer (pH 7.4) in duplicate. Each sample was brought up to 1ml with Hoechst buffer. 1 ml of bisbenzimadazole (diluted 1:1000 with dist $H_2O$) was added and samples were vortexed. Standards were prepared using 134 µg/ml calf thymus DNA diluted 1:10 with Hoechst buffer. Final concentration of DNA ranged from 0.067 to 0.335 µg. All samples and standards were covered for 2 hours and absorbance at 260 mM was determined (LaBarca, C. and Paigan (1980) Anal. Biochem. 102:344–352).

Figure 18:
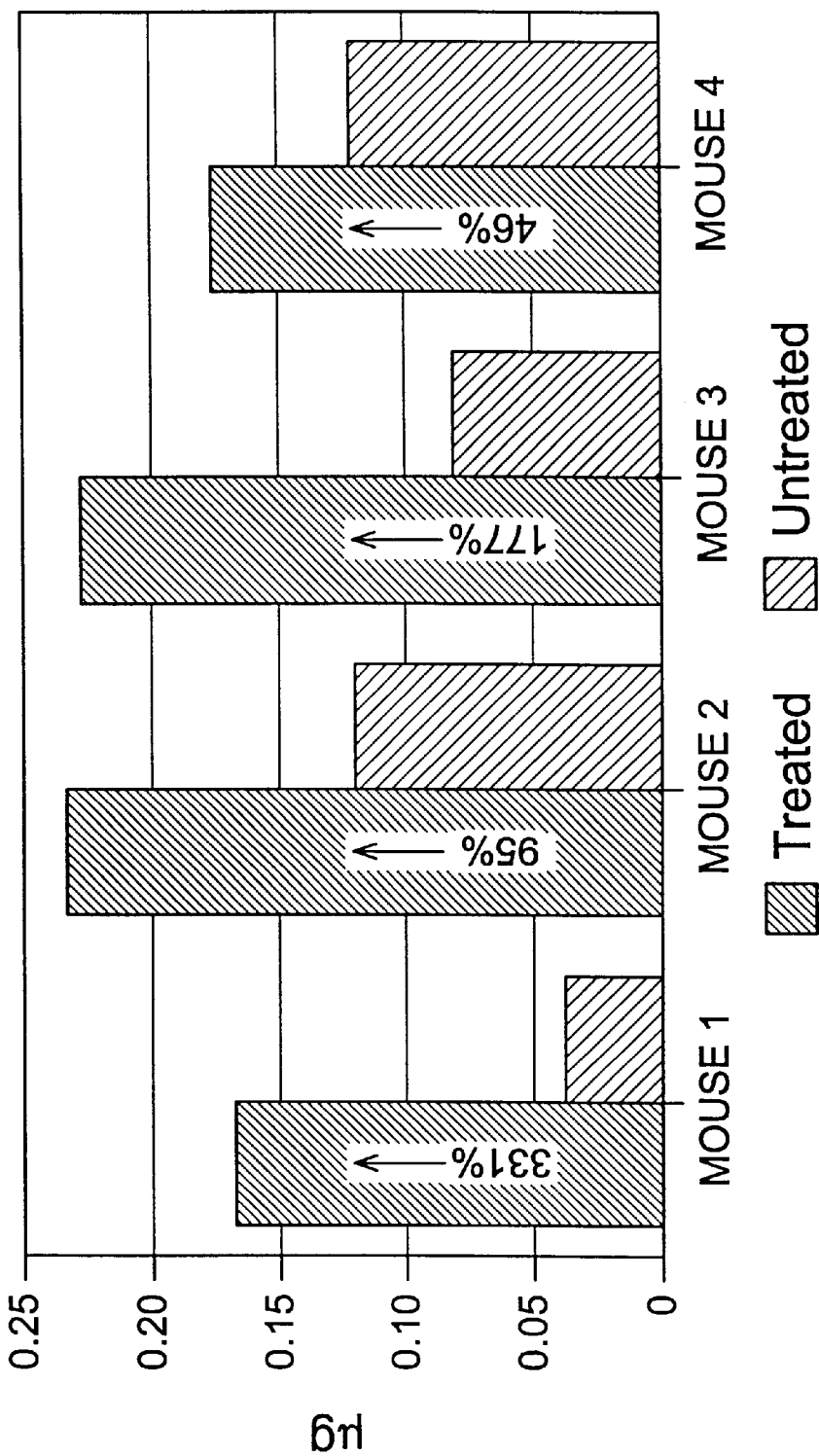
FIG. 18 shows the DNA concentration of CBE-reated and control murine epidermis.

After 5 days of CBE-treatment DNA concentration of all treated skin samples are all higher than untreated skin samples by 46–331% (mean values of four DNA assays; FIG. 18).

Figure 19:
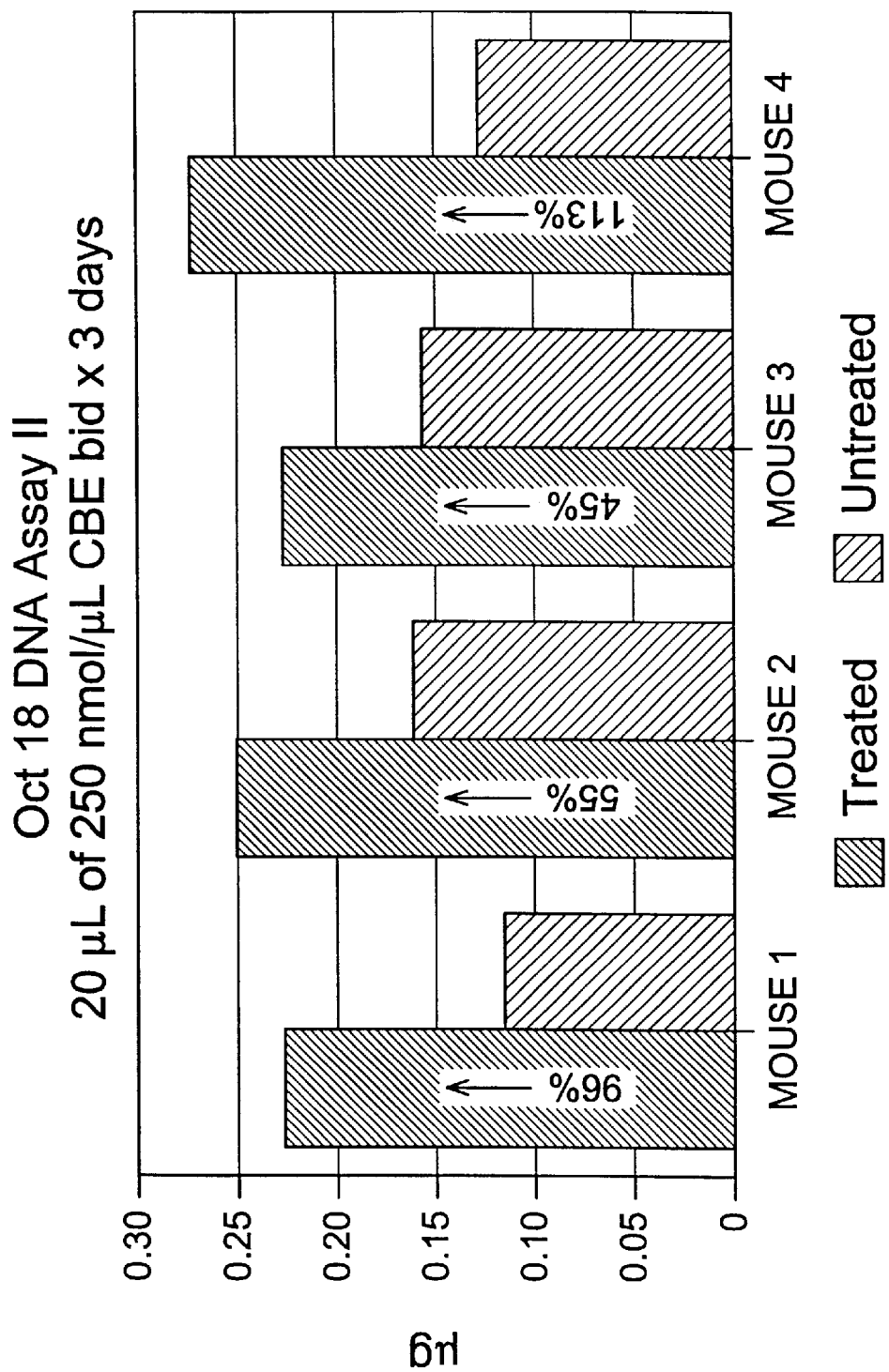
FIG. 19 shows the amount of DNA in CBE-treated and control murine epidermis.

After 3 days of CBE-treatment DNA concentrations of all treated samples are all higher than untreated samples by 45–113% (FIG. 19).

Figure 20:
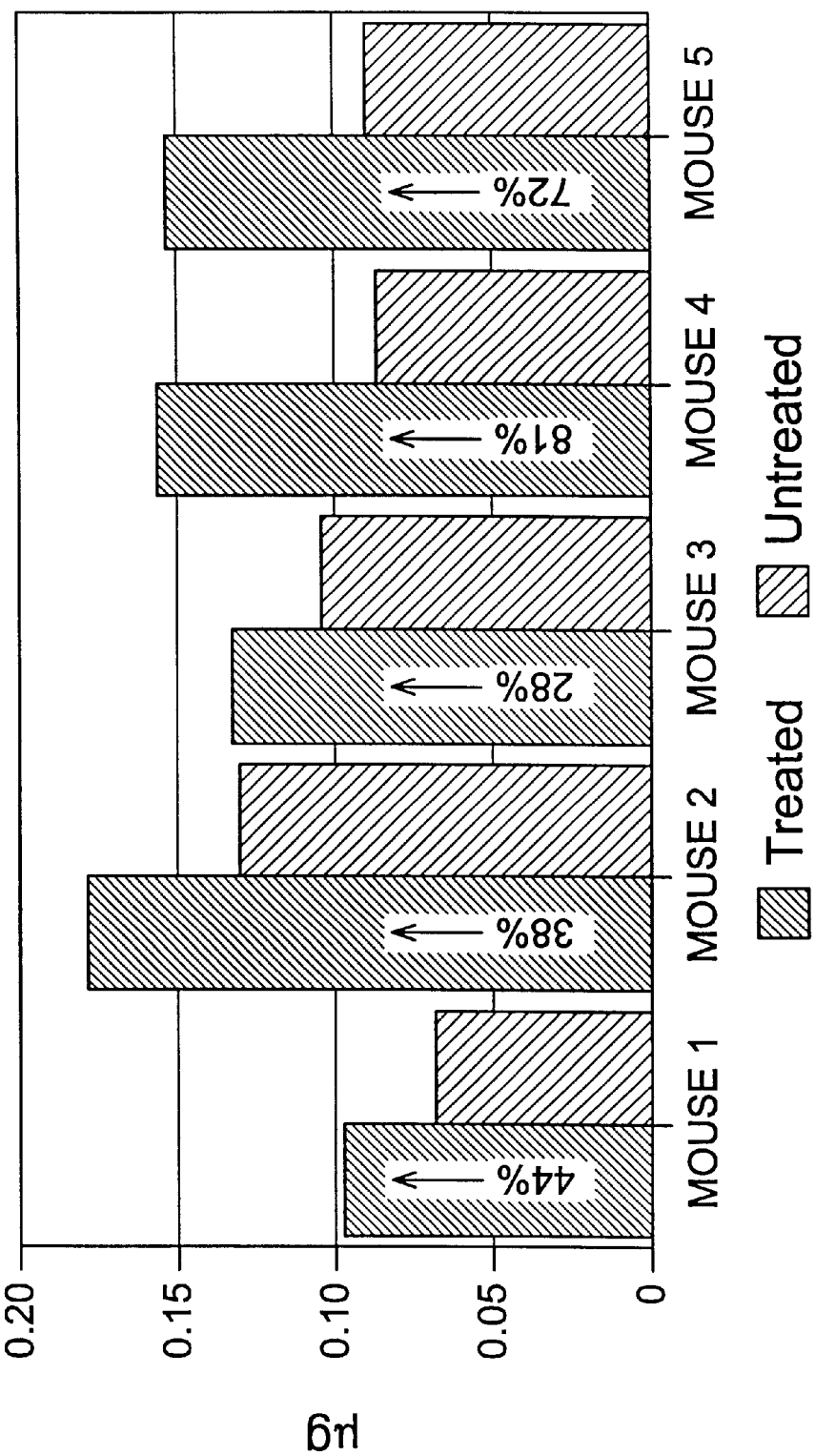
FIG. 20 shows the amount of DNA in another set of CBE-treated and control murine epidermal samples.
Figure 21:
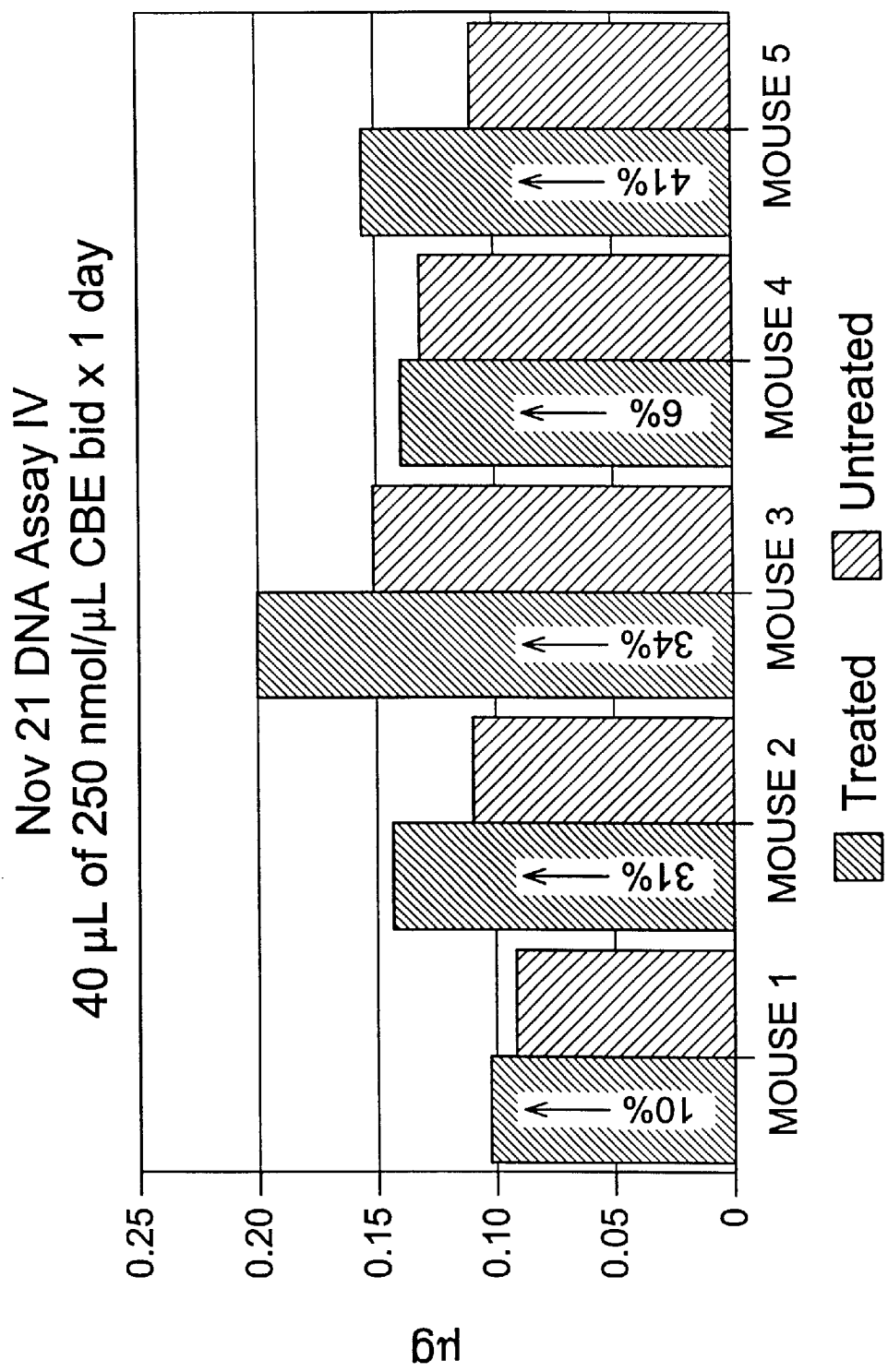
FIG. 21 shows the amount of DNA in CBE-treated and control murine epidermis.

Furthermore as early as 24 hours following CBE treatment, DNA concentrations of the treated samples are all higher than untreated samples by 6–81% (FIGS. 20 & 21). The last two studies (FIGS. 20 & 21) showed an overall lower increase in [$^3$H]-thymidine incorporation in the treated samples compared to the two previous studies due to the short one day period of treatment with CBE.

EXAMPLE 16
Increase in in Epidermal Glucosylceramide in CBE-treated Mice.

The epidermal glucosylceramide content was determined in mice treated with the topical β-glucocerebrosidase inhibitors. Mice were treated with CBE for one day as described in FIG. 22. The mice were sacrificed and whole skin was excised. Subcutaneous fascia and fat were scraped off, and the samples were placed dermis side down onto 10 nM EDTA in PBS-CMF (pH 7.4) and incubated at 37° C. for 40 min. Skin was blotted dry with a tissue and the epidermis was removed by scraping with a surgical blade. The epidermis was minced, placed into microcentrifuge vials, immediately snap frozen and stored in liquid $N_2$ until extracted.

For extraction the tissue was soaked in 7.6 ml Bligh/Dyer extraction media (2 ml chloroform, 4 ml Methanol, 1.6 ml $H_2O$) overnight at room temperature. The following day the tissue was shaken for 20 min. and centrifuged for 10 min. the solvent was removed and the pellet was combined with 7.6 ml Bligh/Dyer media and again shaken and centrifuged. The solvents were combined with solvent from the soaks and filtered through pre-solvent-washed Whatman 43 filter paper, 2 ml chloroform and 2 ml $H_2O$ was added to each 7.6 ml quantity of the filtrate and shaken for 10 min. The samples were then centrifuged and the upper phase discarded. The lower phase was washed with 4 ml chloroform, 4 ml MetOH, and 3.6 ml $H_2O$ (shaken for 10 min and centrifuged). The upper phase was discarded. The lower phase was dried under $N_2$ in a 47° C. water bath. The lipid was resuspended in chloroform and weighed on the Cahn balance.

TLC was performed using 15–20 µg samples and quantitated against standard glycosylceramide and 40 µg sample for sphingolipids (Holleran, W. M. et al. (1993) J. Clin. Invest. 91:1656–1664).

Figure 22:
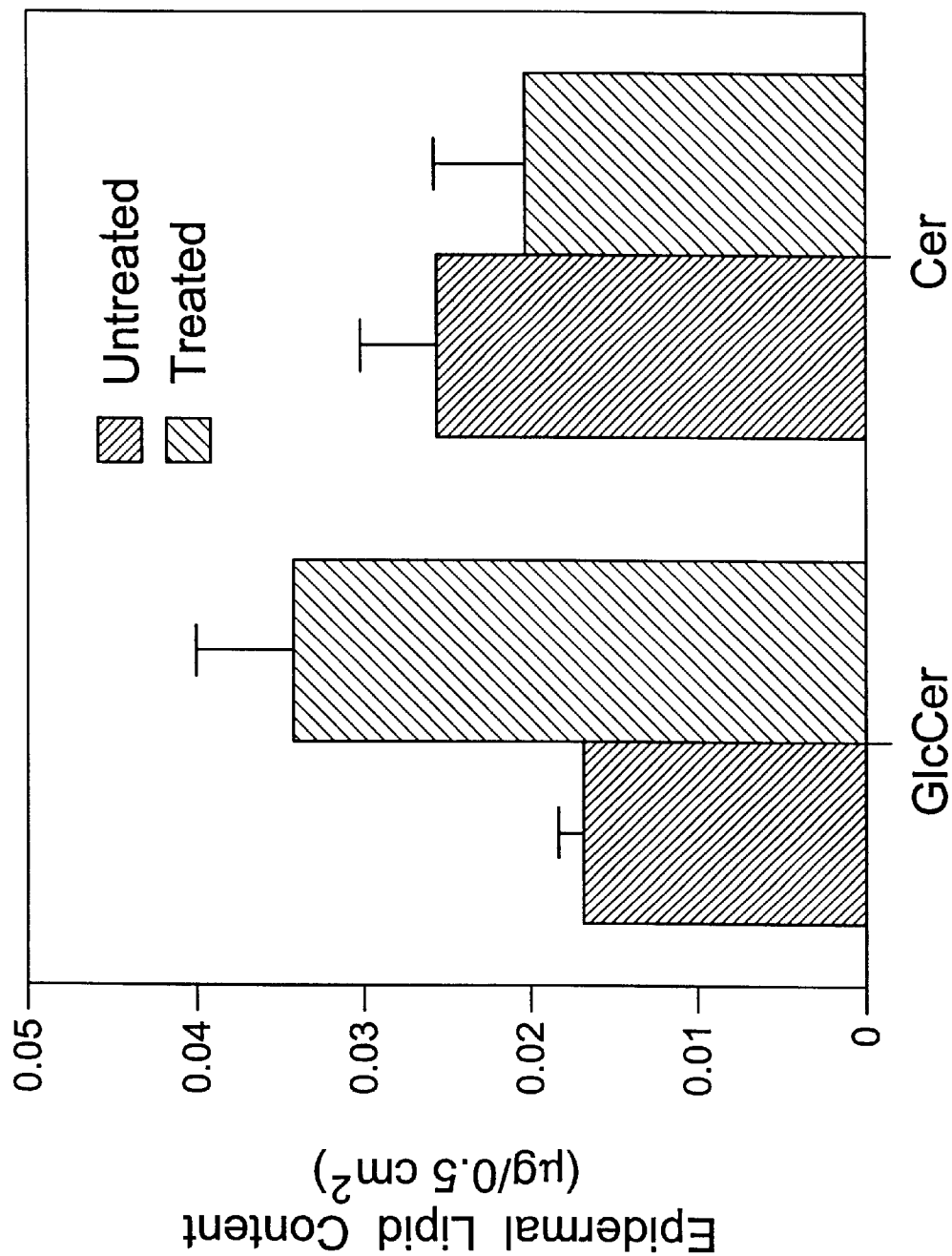
FIG. 22 shows the amount of glucosylceramide and ceramide in CBE-treated epidermis compared with untreated controls.

Glucosylceramide content was invariably increased after one is day of inhibitor applications to hairless mouse skin in vivo (FIG. 22). Thus, the increase in epidermal DNA synthesis and content correlates with increased glucosylceramide content.

Figure 23A:
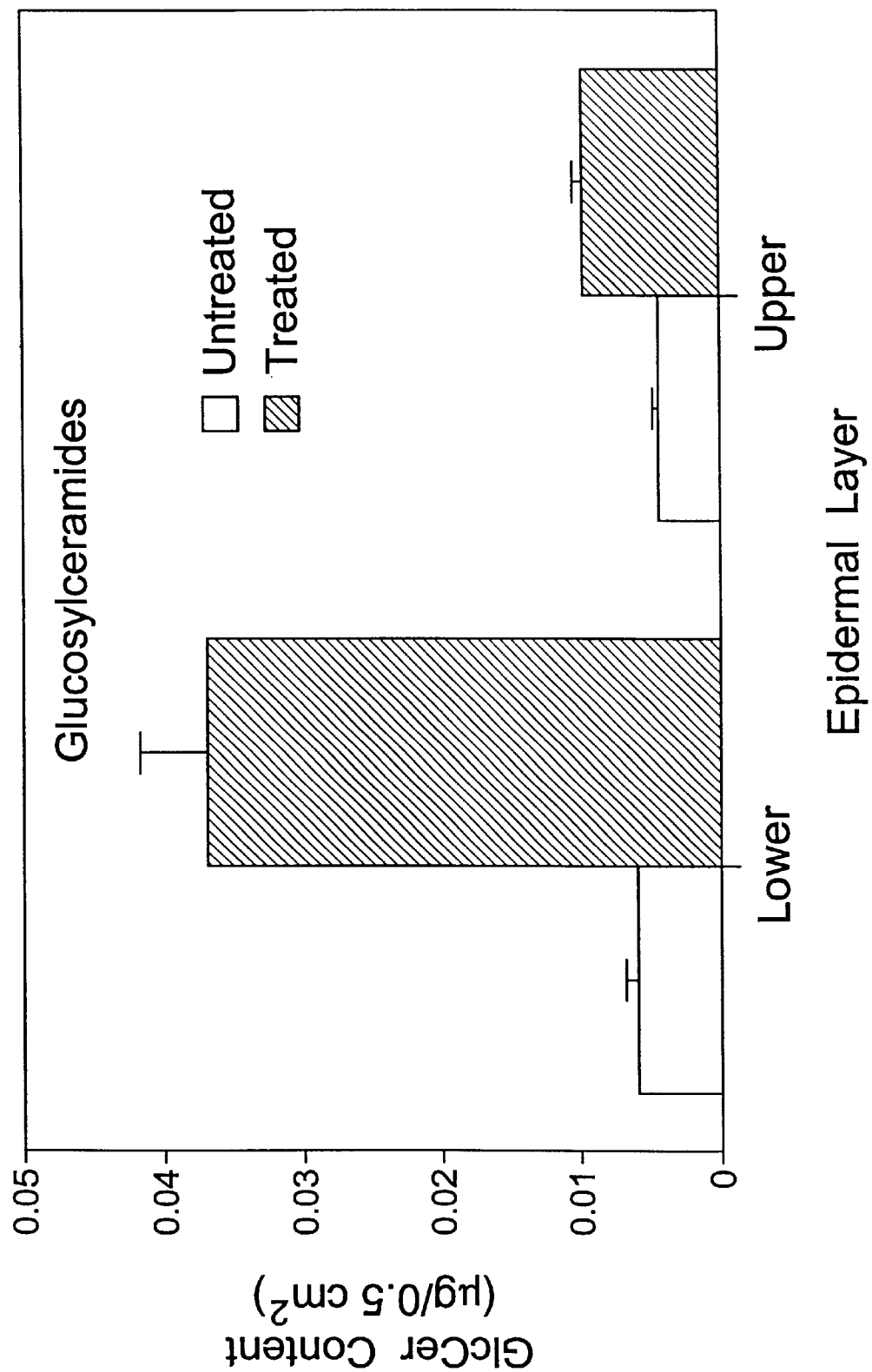
FIG. 23 shows the amount of glucosylceramide and ceramide in upper and lower layers of CBE-treated epidermis.
Figure 23B:
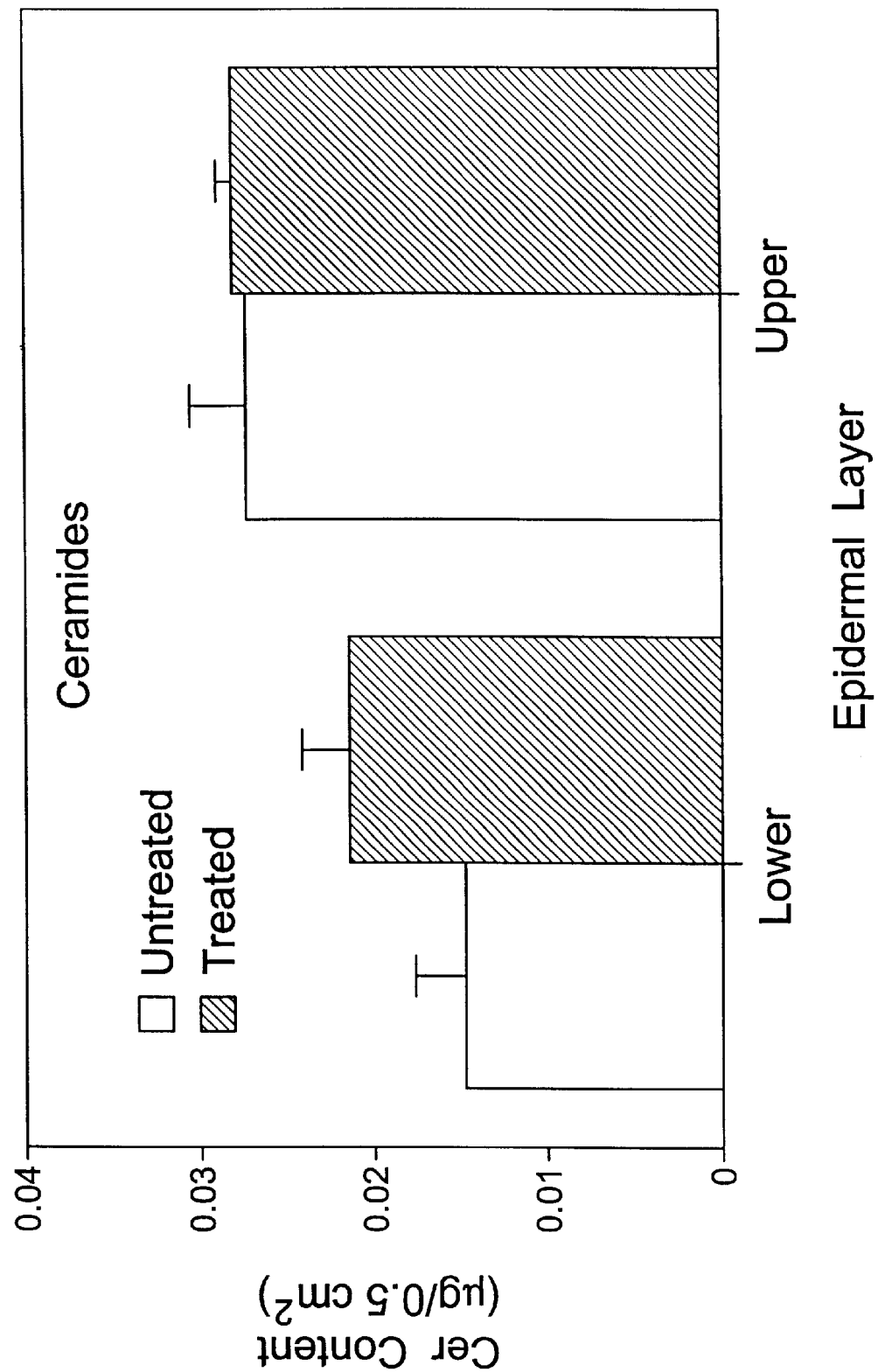

Both glucosylceramide and ceramide content was then determined in lower (stratum basale) and upper (stratum spinosum, stratum granulosum and stratum corneum) epidermis (FIG. 23). Following 24 hours of CBE treatment samples were excised following treatment (as in Example 16). Upper and lower epidermis were separated by soaking tissues in DTT (Proksch, E., Elias, P. M. and Feingold, K. R., Biochim. Biophys. Acta 1083:71–79 (1991). Both upper and lower epidermis showed significant increase in glucosylceramide content after one day of CBE treatment. Ceramide levels were not significantly altered (FIGS. 23A & B).

In FIG. 24 the mice were treated with 20 µl of 250 nmol/µl CBE tid x5d. A 250 mm$^2$ skin sample was taken for this study. The level of glucosylceramide was 34–147% higher in the treated samples.

In FIG. 25 the mice were treated with 40 µl of 250 nmol/µl CBE tid x 3d. A 500 mm$^2$ skin sample was taken in this study. This study showed the same results as the previous lipid study although the concentration of lipids was lower. This may be due to the shorter period of treatment despite an increase in dosage of 40 µg and larger sample size). The level of glucosylceramide was 57–152% higher in the treated samples.

EXAMPLE 17
Effect of Various β-glucosidase Inhibitors on DNA Synthesis.

We next determined whether the topical administration of structurally similar but less efficient β-glucosidase inhibitors would induce epidermal hyperproliferation. Animals were treated topically twice daily with either Conduritol-B-epoxide, Conduritol B (CB), or deoxynojirimycin(dNJM), each at 40 µl of 250 nmol/µl twice daily, as described in Example 10. After 24 hours, [$^3$H]-thymidine was injected intraperitoneally and incorporation of thymidine into DNA was determined (FIGS. 26 A&B). Both CB and DNJM are approximately 10–200 fold less active inhibitors when compared with CBE (Holleran, W. M. et al., J. Clin. Inv. (1992) 33:1201–1209). This reduced activity is a result of the relative availability of these inhibitors to in vivo tissues. Neither CB or DNJM at this concentration induced an increase in DNA synthesis (FIG. 26A), while CBE again demonstrated a potent stimulation of DNA synthesis. These data demonstrate that the effects of CBE are not simply due to an irritant chemical effect as compounds of similar structure (c.f. FIG. 3) with lesser inhibitory activity were not stimulatory.

EXAMPLE 18
Effect of Direct Application of GlcCER and Other Ceramide Analogs on Epidermal DNA Synthesis.

In order to further demonstrate the specificity of the GlcCER effect, we determined the effect of a structural analog of GlcCER, galactosylceramide (GalCER). Animals were treated as described in Example 10.

GlcCER induced a significant increase in DNA synthesis, while the combination of GlcCER with CBE produced an additive effect (FIG. 26B). Neither GalCER nor ceramide (CER) alone at this concentration(c.f. structures in FIGS. 4 and 6) induced an increase in [$^3$H]-thymidine incorporation (FIG. 26B).

These results demonstrate that the replacement or removal of the glucose moiety eliminated the mitogenic effects seen with GlcCER. Thus the effects of GlcCER depend on a relative specificity for glucosyl group at the 3-OH position of the ceramide backbone.

EXAMPLE 19
Effect of Vapor Occlusion on DNA Synthesis.

We next determined whether occlusion with a vapor-impermeable membrane would enhance the effects of a β-glucocerebrosidase inhibitor on epidermal DNA synthesis. Animals were treated as described in Example 10 and groups of animals had their permeability barriers artificially restored using water-vapor impermeable latex wrap. After 24 hrs animals were injected with [$^3$H]-thymidine, and incorporation into DNA was determined (Proksch, et. al., J. Clin. Invest. 87:1668–1673, 1991).

The results from 4 separate studies demonstrate that mice treated with CBE +occlusion had equivalent or higher synthesis rates than animals treated with CBE alone (FIG. 27). Furthermore treatment with CBE, GlcCER and occlusion again resulted in an increased DNA synthesis.

These experiments also specifically address the issue of whether the increase in DNA synthesis is due to increased glucosylceramide content, or whether the increase in DNA synthesis is a consequence of barrier disruption per se (we have published previously that barrier function regulates epidermal DNA synthesis, and that DNA synthesis increases after barrier disruption using acetone extraction(Proksch, et. al., J. Clin. Invest. 87:1668–1673, 1991). Occlusion with a Latex srap inhibits water loss, mimicing the permeability barrier. Thus, if occlusion had prevented the increase in DNA synthesis that followed application of the β-glucocerebrosidase inhibitor or direct injection of GlcCER (see Examples 14, 15,17, 18 above), then this finding would contradict our essential hypothesis; i.e., that it is the increased glucosylceramides which are responsible for the stimulation of epidermal DNA synthesis. As seen in the example above (FIG. 27), occlusion greatly stimulated rather than blocked the increase in epidermal DNA synthesis. This observation proves that the increase in DNA synthesis and content results from the increase in glucosylceramide content (which has been localized further the basal layer, the site where such stimulation must occur).

EXAMPLE 20

Effect of Other Inhibitors on Barrier Recovery.

In order to further evaluate different inhibitors for their ability to alter barrier properties of epithelium, mice were exposed to the β-glucocerebrosidase inhibitor, 4-methylumbelliferyl xyloside (MUX) (Freeze, H. et al., J. Biol. Chem. 268:1618–1627 (1993). MUX was applied topically at concentrations of either 0.5 or 1.0% (wt:vol) in propyleneglycol:ethanol (7:3 vols) to acetone treated skin sites using the protocol in FIG. 28. (MUX was obtained from Sigma Chemical Co., St. Louis, Mo.) With the MUX, we observed a barrier-disrupting effect comparable to the two conduritol compounds (BrCBE and CBE) (Example 10–12). As can be seen, MUX delayed barrier recovery at 2, 4 and 6 hours in a dose-dependent fashion.

These data confirm that several different classes of β-glucocerebrosidase inhibitors produce comparable effects on the epidermal barrier, indicating a common mechanism of action.

What is claimed in letters patent:

1. A method of stimulating epithelial proliferation and enhancing epithelial moisturization and lubrication in a subject, the method comprising administering to the subject an epithelial proliferation stimulating and epithelial moisturization and lubrication enhancing amount of a composition comprising at least one inhibitor of an enzyme having β-glucosidase activity.

2. A method of stimulating epithelial proliferation and enhancing epithelial moisturization and lubrication in a subject, the method comprising administering to the subject a tissue proliferation stimulating and epithelial moisturization and/or lubrication enhancing amount of a composition comprising a glycosphingolipid.

3. A method for enhancing epithelial moisturization and lubrication in a subject, the method comprising administering to the subject an epithelial moisture and lubrication enhancing effective amount of a composition comprising at least one inhibitor of an enzyme having β-glucosidase activity.

4. A method for enhancing epithelial moisturization and lubrication in a subject, the method comprising administering is to the subject an epithelial moisture and lubrication enhancing effective amount of a composition comprising a glycosphingolipid.

5. An in vitro method of stimulating epithelial proliferation and enhancing epithelial moisturization and/or lubrication, the method comprising providing to the cell a cell proliferation stimulating and epithelial moisturization and lubrication enhancing amount of a composition comprising at least one inhibitor of an enzyme having β-glucosidase activity.

6. The method of claim 1 wherein the enzyme is β-glucocerebrosidase.

7. The method of claim 1 wherein the composition further comprises a glycosphingolipid.

8. The method of claim 3 wherein the enzyme is β-glucocerebrosidase.

9. The method of claim 3 wherein the composition further comprises a glycosphingolipid.

10. The method of claim 5 wherein the enzyme is β-glucocerebrosidase.

11. The method of claim 5 wherein the glycosphingolipid is selected from the group consisting of glucosylceramide, and derivatives and analogues thereof.

12. The method of claim 10 wherein the inhibitor of β-glucocerebrosidase is selected from the group consisting of conduritols, N-acylglucosylsphingosine, acylnojiritetrazoles, castanospermines and β-xylosides.

13. The method of claim 6 wherein the inhibitor of β-glucocerebrosidase is selected from the group consisting of conduritols, N-acylglucosylsphingosines, acylnojiritetrazoles, castanospermines and β-xylosides.

14. The method of claim 6 wherein the inhibitor of β-glucocerebrosidase is about 0.01% to 25.0% by weight of the composition.

15. The method of claim 6 wherein the inhibitor of β-glucocerebrosidase is administered at about 1.0 mg to 50.0 mg per gram of body weight.

16. The method of claim 6 wherein the means of administration to the subject is selected from the group consisting of subcutaneous injection, intradermal injection, intraperitoneal injection, intraocular injection, intramuscular injection, intravenous injection, subcutaneous implant, topical application, oral administration, and aerosol inhalant.

17. The method of claim 8 wherein the inhibitor of β-glucocerebrosidase is selected from the group consisting of conduritols, N-acylglucosylsphinosine, acylnojiritetrazoles, castanospermines and β-xylosides.

18. The method of claim 13 wherein the acylnojiritetrazole is selected from the group consisting of D-glucono-1, 5-lactone D-gluconojiritetrazole and D-mannonojiritetrazole.

19. The method of claim 13 wherein the conduritol is selected from the group consisting of conduritol, conduritol-B-epoxide, bromo-conduritol, cyclophellitol, deoxynojirimycin and bromo-conduritol-B-epoxide.

20. The method of claim 13 wherein the β-xyloside is a β-xyloside ester, wherein the ester is C2 through C14.

21. The method of claim 13 wherein the N-acylglucosylsphingosine is selected from the group consisting of N-acylglucosylsphingosine wherein the sphingosine group is C14 to C22 and the acyl group is C2 to C30.

22. The method of claim 20 wherein the xyloside is selected from the group consisting of 4-methyl- β-xyloside, 4-methyl-umbelliferyl-β-xyloside, 4-methyl-β-lactoside, 4-methyl-umbelliferyl-β-lactoside and p-naphthyl-p-β-xyloside.

23. The method of claim 21 wherein the N-acylglucosylsphingosine is selected from the group consisting is of N-hexylglucosylsphingosine and N-octanoylglucosylsphingosine.

24. The method of claim 7 wherein the glycosphingolipid is selected from the group consisting of cerebrosides, gangliosides, sulfatides and globosides.

25. The method of claim 24 wherein the cerebroside is a monohexylceramide.

26. The method of claim 25 wherein the monohexylceramide comprises glucosylceramide and analogues and derivatives thereof.

27. The method of claim 24 wherein the ganglioside is selected from the group consisting of GM1, GM2 and GM3, and derivatives and analogues thereof.

28. The method of claim 1 wherein the subject is a mammal.

29. The method of claim 27 wherein the mammal is a human individual.

30. The method of claim 1 wherein the epithelium is selected fom the group consisting of ocular, otic, pharyngeal, nasal, oral, esophogeal, gastrointestinal and urogenital mucosa.

* * * * *